United States Patent
Asahara et al.

(10) Patent No.: US 10,286,014 B2
(45) Date of Patent: May 14, 2019

(54) METHOD FOR IN VITRO PROLIFERATION OF CELL POPULATION CONTAINING CELLS SUITABLE FOR TREATMENT OF ISCHEMIC DISEASE

(71) Applicants: Foundation for Biomedical Research and Innovation, Hyogo (JP); Tokai University Educational System, Tokyo (JP); StemMed Inc., Hyogo (JP); JUNTENDO EDUCATIONAL FOUNDATION, Tokyo (JP)

(72) Inventors: Takayuki Asahara, Hyogo (JP); Haruchika Masuda, Kanagawa (JP); Rika Tanaka, Tokyo (JP)

(73) Assignees: FOUNDATION FOR BIOMEDICAL RESEARCH AND INNOVATION AT KOBE, Hyogo (JP); TOKAI UNIVERSITY EDUCATIONAL SYSTEM, Tokyo (JP); STEMMED INC., Hyogo (JP); JUNTENDO EDUCATIONAL FOUNDATION, Tokyo (JP)

( * ) Notice: Subject to any disclaimer, the term of this patent is extended or adjusted under 35 U.S.C. 154(b) by 10 days.

(21) Appl. No.: 14/431,791

(22) PCT Filed: Sep. 30, 2013

(86) PCT No.: PCT/JP2013/076618
§ 371 (c)(1),
(2) Date: Mar. 27, 2015

(87) PCT Pub. No.: WO2014/051154
PCT Pub. Date: Apr. 3, 2014

(65) Prior Publication Data
US 2015/0238538 A1    Aug. 27, 2015

(30) Foreign Application Priority Data

Sep. 28, 2012   (JP) ................................. 2012-218206

(51) Int. Cl.
| | |
|---|---|
| *A61K 35/44* | (2015.01) |
| *A61K 35/14* | (2015.01) |
| *A61K 35/28* | (2015.01) |
| *A61K 35/15* | (2015.01) |
| *A61K 35/12* | (2015.01) |
| *C12N 5/071* | (2010.01) |
| *C12N 5/0786* | (2010.01) |

(52) U.S. Cl.
CPC .............. *A61K 35/44* (2013.01); *A61K 35/14* (2013.01); *A61K 35/15* (2013.01); *A61K 35/28* (2013.01); *C12N 5/0645* (2013.01); *C12N 5/0692* (2013.01); *A61K 2035/124* (2013.01); *C12N 2500/84* (2013.01); *C12N 2500/90* (2013.01); *C12N 2501/10* (2013.01); *C12N 2501/125* (2013.01); *C12N 2501/145* (2013.01); *C12N 2501/165* (2013.01); *C12N 2501/2306* (2013.01); *C12N 2501/26* (2013.01); *C12N 2502/28* (2013.01)

(58) Field of Classification Search
None
See application file for complete search history.

(56) References Cited

U.S. PATENT DOCUMENTS

| | | | |
|---|---|---|---|
| 2008/0085555 A1 | 4/2008 | Asahara et al. | |
| 2008/0166327 A1 | 7/2008 | Asahara et al. | |
| 2008/0166751 A1 | 7/2008 | Asahara et al. | |
| 2008/0260703 A1* | 10/2008 | Riordan ................. | A61K 35/15 424/93.7 |
| 2012/0003738 A1 | 1/2012 | Costa et al. | |
| 2012/0100610 A1 | 4/2012 | Mizukami et al. | |
| 2012/0207790 A1* | 8/2012 | Maruyama ........... | C12N 5/0667 424/278.1 |

FOREIGN PATENT DOCUMENTS

| | | | |
|---|---|---|---|
| EP | 2 418 272 | | 2/2012 |
| JP | 2009-55817 | | 3/2009 |
| JP | WO2011043136 | * | 4/2011 |
| WO | 2006/090882 | | 8/2006 |

(Continued)

OTHER PUBLICATIONS

Schmid, M.C. et al. 2007. Myeloid cell trafficking and tumor angiogenesis. Cancer Letters 250: 1-8. specif. pp. 1, 2, 5.*
Fadini, G.P. et al. 2010. Rosuvastatin stimulates clonogenic potential and anti-inflammatory properties of endothelial progenitor cells. Cell Biology International 34: 709-715. specif. p. 709.*
Medina, R.J. et al. Jun. 9, 2011. Myeloid angiogenic cells act as alternative M2 macrophages and modulate angiogenesis through interleukin-8. Molecular Medicine 17(9-10): 1045-1055. specif. pp. 1045, 1046, 1050.*
Olefsky, J.M. et al. 2010. Macrophages, inflammation, and insulin resistance. Annual Review of Physiology 72: 219-246. specif. pp. 220, 237, 238, 239.*

(Continued)

*Primary Examiner* — Renee Claytor
*Assistant Examiner* — Sharon M. Papciak
(74) *Attorney, Agent, or Firm* — Wenderoth, Lind & Ponack, L.L.P.

(57) ABSTRACT

Simplification of a preparation step of a cell population used for the treatment of ischemic diseases, and provision of a cell population that shows more effective treatment are shown. A method of producing a cell population wherein a vascular endothelial progenitor cell and/or an anti-inflammatory macrophage are/is enriched, including cultivating a mononuclear cell derived from bone marrow, cord blood or peripheral blood in a serum-free medium containing stem cell factor, interleukin-6, FMS-like tyrosine kinase 3 ligand, thrombopoietin and vascular endothelial cell growth factor, and proliferating vascular endothelial progenitor cell from the cell; and a cell population obtained by the method are shown.

17 Claims, 11 Drawing Sheets

(56) References Cited

FOREIGN PATENT DOCUMENTS

WO   2006/090886   8/2006
WO   2006/093172   9/2006

OTHER PUBLICATIONS

Asahara, "Basic and clinical studies relating to treatment of ischemic diseases due to transplantation of amplified vascular endothelial progenitor cells cultured ex vivo", Health and Labor Sciences Research Grant (Promotion of clinical application of basic research result), 2006, pp. 1-3, with English translation.
Masuda, "Study of culture system for amplification and differentiation of blood vessel stem cells", Health and Labor Sciences Research Grant (human genome, regenerative medicine etc. research program), 2006, pp. 9-10, with English translation.
Mochida, "Technical development relating to ensured safety and quality of cells and tissues in research of spinal disc regeneration using spinal disc nucleus pulposus cells activated by autologous bone marrow mesenchymal stem cell", 2010 Health and Labor Sciences Research• regenerative medicine practicalization research program, 2012, pp. 14-15, with English translation.
Hur et al., "Identification of a Novel Role of T Cells in Postnatal Vasculogenesis Characterization of Endothelial Progenitor Cell Colonies", Circulation, vol. 116, 2007, pp. 1671-1682.
International Search Report dated Jan. 7, 2014 in International (PCT) Application No. PCT/JP2013/076618.
Extended Supplementary Search Report dated May 3, 2016 in corresponding European Patent Application No. 13842351.2.
First Office Action dated Dec. 5, 2016, in corresponding Chinese Application No. 201380062214.5, with English translation.
Zhou Bin et al., "Neovascularization Potential of Mobilized Peripheral Mononuclear Cells from Diabetes Patients", ACTA Academiae Medicinae Sinicae, vol. 29, No. 2, 2007, pp. 262-267.
Zhang Hongqi et al., "Characterizations and Roles of Endothelial Progenitor Cells in Vascular Biology", Progress of Anatomical Sciences, vol. 12, No. 1, 2006, pp. 79-85.

\* cited by examiner

METHOD FOR IN VITRO PROLIFERATION OF CELL POPULATION CONTAINING CELLS SUITABLE FOR TREATMENT OF ISCHEMIC DISEASE

TECHNICAL FIELD

The present invention relates to a method of proliferating and/or modifying a cell population containing vascular endothelial progenitor cells, which are suitable for the treatment of ischemic diseases, from a mononuclear cell fraction under serum-free culture, a cell population obtained by the method, a production method of a therapeutic agent for ischemic diseases, which contains the cell population, and the like.

BACKGROUND ART

Targeting ischemic cardiac diseases, a bone marrow mononuclear cell transplantation therapy and a cell transplantation therapy using endothelial progenitor cells (EPC) by collecting peripheral-blood stem cells have been applied in recent years. Therefore, a technique for cultivating a large amount of EPC has been particularly desired. The in vitro proliferation method of vascular endothelial progenitor cell from CD34 and/or CD133 positive cells developed by the present inventors has made it possible to provide an efficient culture technique of EPC (patent document 1). The method of analyzing dynamics in the differentiation of vascular endothelial cells invented by the present inventors has clarified the presence of endothelial cell-like large colony (differentiated EPC colony) forming cell and endothelial cell-like small colony (undifferentiated EPC colony) forming cell, which has enabled prediction and understanding of the treatment effect of cell transplantation (patent document 2). In addition, the present inventors have shown a method of efficiently proliferating CD34 and/or CD133 positive cells from bone marrow mononuclear cells (patent document 3).

On the other hand, it has also been reported that the revascularization capacity of EPC is enhanced by cocultivating EPC and CD3 positive-CD31 positive cells called angiogenic T cells and present in a CD34 negative cell population, and the CD34 negative cell population is suggested to contain a cell that enhances the ability of EPC (non-patent document 1).

DOCUMENT LIST

Patent Documents patent document 1: WO 2006/090882
patent document 2: WO 2006/090886
patent document 3: WO 2006/093172

Non-Patent Document non-patent document 1: Circulation 2007, 116: 1671-1682

SUMMARY OF THE INVENTION

Problems to be Solved by the Invention

As shown in the above-mentioned documents, the present inventors developed a new EPC culture technique, but the EPC preparation step thereof still requires time and cost since CD34 and/or CD133 positive cells need to be sorted from peripheral blood and the like. As in the above-mentioned non-patent document 1, moreover, a cell capable of enhancing the capacity of EPC may be present in the CD34 negative cell population. Thus, as in the above-mentioned patent document 3, the conditions for cultivating mononuclear cells were studied without sorting the CD34 and/or CD133 positive cells to obtain EPC fraction, or by mixing CD34 positive cells and CD34 negative cells at a give ratio. As a result, it was verified that differentiated (large-type) EPC colony forming cells considered to have high potency to differentiate into vascular endothelial cells are efficiently proliferated by the method of the present invention, and surprisingly that the culture or cell population obtained by the method are superior to the culture or cell population obtained by culturing CD34 and/or CD133 positive cells in an angiogenesis action as well as tissue repairability, since they have an inflammation suppressive action together with superior vascular endothelium formability, and effective for the treatment of ischemic diseases.

Accordingly, the problem of the present invention is to simplify a preparation step of a cell population used for the treatment of ischemic diseases, and provide a cell population that shows more effect by the treatment. More specifically, the problem is to provide a means for the proliferation of a cell population including not only revascularizative cells: specifically, differentiated EPC colony forming cells with high angiogenesis ability, but also anti-inflammatory/immune tolerance inducing cells: specifically, M2 macrophage converted to be anti-inflammatory, T lymphocyte subset, regulatory T cells, by simplification of a cell sorting step after collection of bone marrow, cord blood and peripheral blood.

Means of Solving the Problems

In view of the above-mentioned problems, the present inventors studied culture conditions capable of achieving differentiation/proliferation of these cells into a cell population contributing to the angiogenesis, without sorting mononuclear cells in vitro, or by mixing CD34-sorted, unsorted cells. As a result, they have succeeded in efficient proliferation of a cell population containing EPC in vitro by cultivating mononuclear cells in a serum-free culture medium containing a factor selected from the group consisting of (1) a stem cell factor (SCF), (2) interleukin-6 (IL-6), (3) FMS-like tyrosine kinase 3 ligand (FL) and (4) thrombopoietin (TPO) and (5) a vascular endothelial growth factor (VEGF). The cell population containing EPC is characterized in that it particularly contains EPC and anti-inflammatory M2 macrophage, and also contains anti-inflammatory T lymphocyte subset and regulatory T cells. Therefore, it has been clarified that this cell population not only shows vascular development but also has an anti-inflammatory action. Furthermore, the present inventors have clarified that a cell population having a similar function can also be obtained in cell populations collected from not only healthy individuals but also diabetes patients.

Particularly in mononuclear cells used for culture, it has been clarified that a cell population showing a markedly high revascularization capacity can be obtained when CD34 positive cells and negative cells are cultured at a given ratio.

Accordingly, the present invention provides the following:

[1] A cell population obtained by culturing a mononuclear cell derived from bone marrow, cord blood or peripheral blood in a serum-free medium containing stem cell factor, interleukin-6, FMS-like tyrosine kinase 3 ligand, thrombopoietin and vascular endothelial cell growth factor.

[2] A cell population obtained by culturing a mononuclear cell derived from bone marrow, cord blood or peripheral blood in a serum-free medium, wherein vascular endothelial progenitor cell and anti-inflammatory macrophage are enriched.

[3] The cell population of the above-mentioned [1], comprising a vascular endothelial progenitor cell and an anti-inflammatory macrophage.

[4] The cell population of the above-mentioned [2] or [3], wherein the vascular endothelial progenitor cell is a differentiated EPC colony forming cell.

[5] The cell population of any of the above-mentioned [2]-[4], wherein the anti-inflammatory macrophage is M2 macrophage.

[6] A method of producing a cell population wherein a vascular endothelial progenitor cell and/or an anti-inflammatory macrophage are/is enriched, comprising cultivating a mononuclear cell derived from bone marrow, cord blood or peripheral blood in a serum-free medium containing stem cell factor, interleukin-6, FMS-like tyrosine kinase 3 ligand, thrombopoietin and vascular endothelial cell growth factor.

[7] The method of the above-mentioned [6], wherein the vascular endothelial progenitor cell is a differentiated EPC colony forming cell.

[8] The method of the above-mentioned [6] or [7], wherein the anti-inflammatory macrophage is M2 macrophage.

[9] A therapeutic agent for an ischemic disease, comprising the cell population of any of the above-mentioned [1]-[5].

[10] The therapeutic agent of the above-mentioned [9], wherein the ischemic disease is a disease cured by angiogenesis.

[11] A therapeutic agent for refractory ulcer or a diabetes-associated disease, comprising the cell population of any of the above-mentioned [1]-[5].

Effect of the Invention

Transplantation of the cell population proliferated by the present invention improved blood flow and necrosis improvement rate of ischemic diseases. The present inventors further studied these effects and concluded that the present invention is useful for both qualitatively and quantitatively producing an endothelial lineage cell, and provides a useful method for cell transplantation therapy targeting vascular disorders such as ischemic diseases and the like.

In particular, according to the present invention, cell population showing high revascularization capacity in both quality and amount can be afforded even in patients with deteriorated revascularization capacity such as diabetes patients and, due to the presence of anti-inflammatory cells, inflammation is suppressed also in cell transplantation. Therefore, the present invention is extremely useful as a cell transplantation therapy.

DESCRIPTION OF EMBODIMENTS

Figure 1:
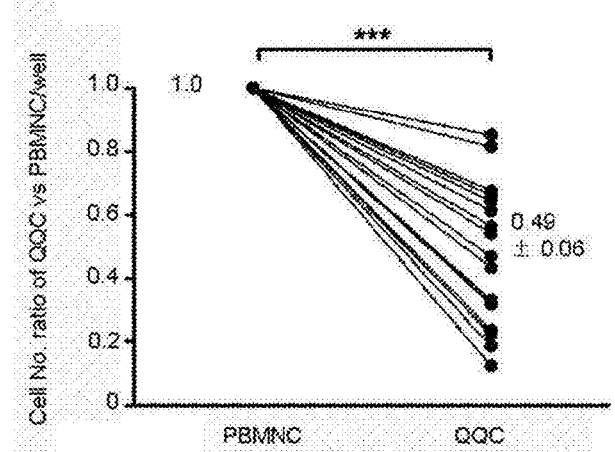
FIG. 1 shows ratios of cells (Quality and Quantity Cell; hereinafter QQC) obtained by seeding peripheral blood mononuclear cells (hereinafter PBMNC) at $2\times10^6$ cells, and culturing for 7 days in the serum-free medium in the present invention relative to the cell number at the time of start of the culture, wherein *** show a significant difference (P<0.001) relative to the targets shown in the Figure.

The present invention provides a method of growing a cell population containing vascular endothelial progenitor cells in vitro, particularly a method of growing a cell population wherein vascular endothelial progenitor cell and anti-inflammatory macrophage are enriched, and a cell population (particularly cell population wherein vascular endothelial progenitor cell and anti-inflammatory macrophage are enriched) for cell transplantation, which is obtained by the method.

The mononuclear cell used in the present invention is a generic term of cells having a circular shaped core and contained in peripheral blood, bone marrow, cord blood and the like, and includes lymphocyte, monocyte, macrophage, vascular endothelial progenitor cell, hematopoietic stem cell and the like. The mononuclear cell also includes CD34 and/or CD133 positive cells. Mononuclear cell is obtained by collecting bone marrow, cord blood or peripheral blood from an animal, subjecting same to, for example, density gradient centrifugation method and extracting the fraction. While the density gradient centrifugation method is not particularly limited as long as the mononuclear cell fraction is formed, Histopaque-1077 (Sigma-Aldrich) is preferably used.

The mononuclear cell used in the present invention is highly characterized in that the obtained mononuclear cell can be directly used for the cell culture mentioned below, without sorting (positive sorting) the CD34 and/or CD133 positive cells.

The animal species from which the cell used in the present invention is derived means a mammal in general including human, to whom the cell transplantation therapy for a disease such as ischemic cardiac diseases and the like is applied. However, in view of the object of the present invention, i.e., clinical application, it is preferably human.

Stem cell factor (SCF) to be used in the present invention is a glycoprotein with about 30,000 of molecular weight, consisting of 248 amino acids. While there exist a soluble form and a membrane-bound form due to alternative splicing, SCF used in the present invention may be of any form, as long as it is useful for cultivation of EPC and the like. It is preferably of a soluble form. While the derivation and the like of SCF are not particularly limited, a recombinant expected to ensure a stable supply is preferable, and a human recombinant is particularly preferable. Commercially available ones are known. The concentration of SCF in the serum-free culture medium varies depending on the kind of SCF to be used, and is not particularly limited as long as it is useful for cultivation of EPC and the like. When human recombinant SCF is used, the concentration is, for example, 10-1000 ng/mL, preferably 50-500 ng/mL, more preferably about 100 ng/mL.

Interleukin-6 (IL-6) to be used in the present invention is a glycoprotein with 210,000 of molecular weight, isolated as a factor introducing terminal differentiation of a B cell into an antibody-producing cell, and known to be involved in immune response, proliferation and differentiation of a hematopoietic lineage or neural lineage cell, acute-phase reaction and the like. While IL-6 to be used in the present invention can be appropriately selected, when it is used for culturing human EPC and the like, human IL-6 is preferable, and a recombinant expected to ensure a stable supply is particularly preferable. Commercially available ones are known. The concentration of IL-6 in the serum-free culture medium varies depending on the kind of IL-6 to be used, and is not particularly limited as long as it is useful for cultivation of EPC and the like. When human recombinant IL-6 is used, the concentration is, for example, 1-500 ng/mL, preferably 5-100 ng/mL, more preferably about 20 ng/mL.

FMS-like tyrosine kinase 3 ligand (FL) to be used in the present invention is known as a ligand of a receptor tyrosine kinase that plays an important role in the initial hemopoietic regulation. While some products resulting from alternative splicing are known, they are reported to stimulate the growth of a hematopoietic lineage stem cell. FL to be used in the present invention may be any type of FL as long as it is useful for cultivation of EPC and the like. Commercially available ones are known. The concentration of FL in the serum-free culture medium varies depending on the kind of FL to be used, and is not particularly limited as long as it is useful for cultivation of EPC and the like. When human recombinant Flt-3 ligand is used, the concentration is, for example, 10-1000 ng/mL, preferably 50-500 ng/mL, more preferably about 100 ng/mL.

Thrombopoietin (TPO) to be used in the present invention is a kind of hematopoietic cytokine, and known to specifically act on the process of producing megakaryocyte from hematopoietic stem cell to promote production of megakaryocyte. While the derivation and the like of TPO to be used in the present invention are not particularly limited, a recombinant expected to ensure a stable supply is preferable, and a human recombinant is particularly preferable. Commercially available ones are known. The concentration of TPO in the serum-free culture medium varies depending on the kind of TPO to be used, and is not particularly limited as long as it is useful for cultivation of EPC and the like. When human recombinant TPO is used, the concentration is, for example, 1-500 ng/mL, preferably 5-100 ng/mL, more preferably about 20 ng/mL.

Vascular endothelial growth factor (VEGF) which can be used in the present invention is a growth factor specifically acting on EPC, and known to be mainly produced in a perivascular cell. Several kinds of VEGF proteins having different sizes are produced by alternative splicing. The VEGF to be used in the present invention may be any type of VEGF as long as it enables colony formation of EPC. It is preferably VEGF165. While the derivation and the like of VEGF are not particularly limited, a recombinant expected to ensure a stable supply is preferable, and a human recombinant is particularly preferable. Commercially available ones are known. The concentration of VEGF in the serum-free culture medium varies depending on the kind of VEGF to be used, and is not particularly limited as long as it is useful for cultivation of EPC and the like. When human recombinant VEGF165 is used, the concentration is, for example, about 5-500 ng/mL, preferably about 20-100 ng/mL, more preferably about 50 ng/mL.

It is preferable to use various factors to be added to the serum-free culture medium of the present invention, which have been derived from the same species of animal as the animal from which the mononuclear cell is derived. By unifying the derivation of the mononuclear cell and various factors, a cell culture suitable for allogeneic transplantation such as allograft and the like can be obtained. In addition, using a mononuclear cell derived from an individual who intends to undergo a cell transplantation, a cell culture suitable for syngeneic transplantation can also be obtained. In this way, since a cell population containing EPC and the like can be cultured in an environment completely free of a component derived from an animal of a different species, the obtained cell culture is advantageous in that a risk of infection and rejection on transplantation and the like can be avoided.

Each of the above-mentioned components is dissolved in a serum-free culture medium to a given concentration, or a concentrated solution of each component (stock solution) is prepared in advance and diluted with a serum-free culture medium to a given concentration, whereby the serum-free culture medium of the present invention to be used for the in vitro expansion of cell population containing vascular endothelial progenitor cells can be prepared. For example, the serum-free culture medium of the present invention can be prepared by dissolving the necessary components in a commercially available serum-free culture medium to given concentrations and sterilizing the medium by filtration and the like, or aseptically adding the stock solutions sterilized by filtration and the like to a commercially available serum-free culture medium to dilute them. Sterilization by filtration can be performed according to a method generally employed in the art. For example, it is performed using 0.22 μm or 0.45 μm of Millipore filter and the like.

As the "serum-free culture medium" to be used in the present invention, any medium generally used in the art can be utilized. For example, a serum-free culture medium known as a medium for growth of hematopoietic stem cells can be used. As the basal medium used as the serum-free culture medium, for example, DMEM, MEM, IMDM and the like can be mentioned.

The serum-free medium of the present invention contains one or more, preferably not less than 3, more preferably all, factors selected from the group consisting of SCF, IL-6, FL, TPO and VEGF. Accordingly, the serum-free culture medium used in the cultivation method of the present invention may contain, for example, a) SCF, b) IL-6, c) FL, d) TPO, e) VEGF, f) a combination of SCF and IL-6, g) a combination of SCF and FL, h) a combination of SCF and TPO, i) a combination of SCF and VEGF, j) a combination of IL-6 and FL, k) a combination of IL-6 and TPO, l) a combination of IL-6 and VEGF, m) a combination of FL and TPO, n) a combination of FL and VEGF, o) a combination of TPO and VEGF, p) a combination of SCF, IL-6 and FL, q) a combination of SCF, IL-6 and TPO, r) a combination of SCF, FL and TPO, s) a combination of SCF, FL and VEGF, t) a combination of IL-6, FL and TPO, u) a combination of IL-6, FL and VEGF, v) SCF, IL-6, FL and TPO, w) a combination of SCF, IL-6, FL and VEGF, x) a combination of IL-6, FL, TPO and VEGF, and y) a combination of SCF, IL-6, FL, TPO and VEGF.

The serum-free medium of the present invention more preferably contains-SCF, IL-6, FL, TPO and VEGF. It more preferably contains about 50 ng/mL of VEGF, about 100 ng/mL of SCF, about 20 ng/mL of IL-6, 100 ng/mL of FL, and about 20 ng/mL of TPO.

A mononuclear cell can be cultured in a serum-free culture medium containing the aforementioned factors by adding a cell suspension containing the mononuclear cell to the serum-free culture medium containing the aforementioned factors. As the cell suspension, a body fluid itself containing a mononuclear cell (e.g., bone marrow fluid, cord blood, peripheral blood) can also be used. The cultivation conditions for a mononuclear cell are not particularly limited, and those generally employed in the art can be utilized. For example, cultivation is performed under a 5% $CO_2$ atmosphere at 37° C. for not less than 7 days (e.g., not less than 10 days). The concentration of a mononuclear cell in a serum-free culture medium is not particularly limited as long as it allows cultivation of the EPC and the like. For example, it is about $0.5\text{-}10\times10^5$ cells/ml, more preferably about $1\text{-}5\times10^5$ cells/ml, most preferably about $3\text{-}4\times10^5$ cells/ml.

The cell population in the present invention is a generic term for cells obtained by culturing mononuclear cells in a serum-free medium containing the aforementioned factors, and is a cell population containing, together with EPC, at least one of vascular endothelial cell, anti-inflammatory macrophage, angiogenic and antifibrotic cells. Also, even mononuclear cells cultured in a medium not containing the aforementioned factors are considered to provide similar effects as long as the vascular endothelial cell, anti-inflammatory macrophage, angiogenic and antifibrotic cells are dominantly proliferated therein together with the above-mentioned EPC.

As the cell population in the present invention, a cell population containing a CD206 positive cell population and a CD34 positive cell population is preferable, and a cell population showing high expression of these is preferable. Specifically, it is preferably a cell population containing differentiated EPC and anti-inflammatory macrophages to be described later is desirable, and a cell population containing a more number of these cell populations, namely, a cell population enriched in these cell populations is more desirable.

Here, the cell population enriched in EPC and/or anti-inflammatory macrophage means that the proportion of each cell in the whole mononuclear cells after culture in a serum-free medium containing the above-mentioned factors increases to not less than 2-fold, preferably not less than 4-fold, more preferably not less than 5-fold, as compared to the respective proportions in the whole mononuclear cells before culture. Since the ratio of EPC and anti-inflammatory macrophages is significantly higher in the cell population obtained by the culture method of the present invention than that of the original mononuclear cells, angiogenesis is significantly promoted and the effect of suppressing inflammation is afforded.

EPC used in the present invention is not particularly limited as long as it is an undifferentiated cell that can be a vascular endothelial cell. Based on the degree of differentiation, EPC can be divided into two kinds of colonies having different sizes, namely, a differentiated EPC colony (CFU-Large cell like EC, also referred to as large EPC colony) mainly including cells with a diameter of 20-50 µm and an undifferentiated EPC colony (CFU-small cell like EC, also referred to as small EPC colony). An undifferentiated (small-type) EPC colony that appears in an early stage is an EPC colony in an early differentiation stage with superior proliferative capacity, and differentiated (large-type) EPC colony that appears in a later stage is an EPC colony in a late differentiation stage with superior vascular development (e.g., Masuda H. et al., Circulation Research, 109: 20-37 (2011)). The EPC contained in the cell population obtained by the present invention contains almost equivalent number of undifferentiated EPC colony forming cells but a significantly increased number of differentiated EPC colony forming cells as compared to the case with sorting for CD34/CD133. It is preferable to contain the same number of undifferentiated EPC forming cells as compared to the case with selection for CD34/CD133 and differentiated EPC colony forming cells in not less than 2-fold thereof. It is more preferable to contain the same number of undifferentiated EPC colony forming cells as compared to the case with selection for CD34/CD133 and differentiated EPC colony forming cells in 4-fold thereof, more preferably 5-fold thereof.

The anti-inflammatory macrophages contained in the cell population obtained by the present invention are CD206-positive, anti-inflammatory and contribute to angiogenesis and repair. Preferred are M2 macrophages, more preferred are CD206 positive M2 macrophages. The cell population obtained by the present invention contains these cells together with vascular endothelial precursor cells, wherein the ratio of the anti-inflammatory macrophages in the cell population generally increases to not less than 2-fold, preferably not less than 4-fold, as compared to unsorted mononuclear cells.

The unexpected method of cultivating unsorted mononuclear cells in a serum-free medium containing the aforementioned factors enables promotion of differentiation of undifferentiated EPC colony forming cell into differentiated EPC colony forming cell, or proliferation thereof, promotion of differentiation or proliferation of blood-lineage cell anti-inflammatory macrophage, or suppression of differentiation or proliferation of inflammatory macrophage.

Promotion of differentiation of undifferentiated EPC colony forming cell obtained by cultivating unsorted mononuclear cells in a serum-free medium containing the aforementioned factors into differentiated EPC colony forming cells or proliferation of differentiated EPC colony forming cells can be confirmed by, for example, measuring the vascular endothelial progenitor cell colony formability of the obtained cell suspension.

The vascular endothelial progenitor cell colony-forming ability can be determined using a methylcellulose medium containing a physiologically active substance, specifically vascular endothelial growth factor (VEGF) and basic fibroblast growth factor (bFGF), preferably further containing 1 or not less than 2, preferably not less than 3, more preferably all, factors selected from the group consisting of stem cell factor (SCF), interleukin 3 (IL-3), insulin growth factor (IGF) and epithelial growth factor (EGF) in addition to the above-mentioned factors, and further containing a serum and/or heparin as necessary. Particularly preferably, vascular endothelial progenitor cell colony is formed by cultivation in a methylcellulose medium containing about 30% serum, about 50 ng/mL VEGF, about 100 ng/mL SCF, about 20 ng/mL IL-3, about 2 U/mL heparin, about 50 ng/mL b-FGF, about 50 ng/mL EGF and about 50 ng/mL IGF, under a 5% $CO_2$ atmosphere at 37° C. generally for not less than 10 days, for example, for 14-18 days or longer. While formation of colony can be visually confirmed, whether or not the obtained colony indeed consists of vascular endothelial progenitor cell is determined by confirming the ability of acetylated LDL (acLDL) uptake, bindability with UEA-1 lectin, expression of VE-cadherin, KDR, vWF (e.g., by RT-PCR or fluorescence immunohistochemical analysis) and the like. For example, when a colony is double-stained with DiI-labeled acetylated LDL (acLDL-DiI) (Biomedical Technologies) and FITC-labeled UEA-1 lectin (UEA-1 lectin-FITC) (Vector Lab), the colony is double-stained in the case of vascular endothelial progenitor cell.

The vascular endothelial progenitor cell colony-forming ability can also be determined using a commercially available kit. As such kit, for example, a kit manufactured by STEMCELL Technology, Inc. (catalog No. H4236) is commercially available. Using the medium of the kit supplemented with each of the aforementioned factors, the EPC colony-forming ability can be conveniently determined.

Differentiation or proliferation of anti-inflammatory macrophages or inflammatory macrophages can be measured by, for example, labeling CD206 (for anti-inflammatory macrophages) and CCR2 (for inflammatory macrophages) with an antibody having affinity therefor, followed by flow cytometer analysis.

Alternatively, the cell population obtained by the present invention may further contain anti-inflammatory Th2 cells and regulatory T cells. Therefore, the cell population obtained by the present invention may also be a cell population containing, in addition to EPC and anti-inflammatory macrophages, enriched anti-inflammatory Th2 cells and regulatory T cells.

Also in these cell populations, the proportion of each cell to the whole cells increases to generally not less than 2-fold, preferably not less than 4-fold, more preferably not less than 5-fold, as compared to the proportions before culture.

The cell population obtained by the present invention preferably contains differentiated EPC colony forming cells, more preferably differentiated EPC colony forming cells and anti-inflammatory macrophages (CD206 positive M2 macrophage). The cell population is extremely effective since it not only develops blood vessels but also suppresses inflammation in an inflammatory site, for example, ulcer and the like.

The present invention further provides a method of preparing vascular endothelial cells, which includes differentiating vascular endothelial progenitor cells obtained by cultivating unsorted mononuclear cells in a serum-free medium containing the aforementioned factors into vascular endothelial cells. Vascular endothelial progenitor cell can be differentiated into vascular endothelial cell by a method known per se. For example, a method using EBM-2, EGM2V Single Quots (Clonetics Inc.), autologous serum and the like can be mentioned.

The cells such as EPC and the like contained in the cell population of the present invention can be appropriately isolated and/or purified. For example, CD34 and CD133 as a cell surface marker of hemangioblast, KDR as a cell surface marker of EPC, KDR and vascular endothelial cadherin as a surface marker of vascular endothelial cell, and CD206 as a surface marker of anti-inflammatory macrophage are known. Therefore, desired cells can be separated by applying cells to a cell separation method using a substance (e.g., antibody) having affinity to these cell surface markers. As such cell separation method, for example, magnetic cell sorting method (MACS) and fluorescent cell sorting method (FACS) can be mentioned.

The present invention is characterized by proliferation of EPC including differentiated EPC colony forming cell, anti-inflammatory macrophage, angiogenic and antifibrotic cells by cultivating mononuclear cells, obtained without CD34 and/or CD133 positive sorting, in a serum-free medium containing the aforementioned factors.

In more detail, when mononuclear cells after CD34 positive sorting are cultivated by the culture method of the present invention, undifferentiated EPC colony forming cells alone are proliferated; however, when unsorted mononuclear cells are used, undifferentiated EPC colony forming cells as well as differentiated EPC colony forming cells are proliferated, and further, anti-inflammatory macrophages are also proliferated. Furthermore, anti-inflammatory Th2 cells and regulatory T cells are also proliferated.

The present invention also provides a therapeutic agent for ischemic diseases.

Since the cell population which is the active ingredient of the agent of the present invention contains differentiated EPC colony forming cells and anti-inflammatory macrophages, the therapeutic agent of the present invention can be applied to diseases treatable by angiogenesis. That is, the therapeutic agent of the present invention can be used for the treatment of vascular disorders by practical cell transplantation. Examples of the "disease treatable by angiogenesis" include ischemic diseases (e.g., ischemic cardiac diseases such as myocardial infarction, angina pectoris and the like, limb ischemia such as limb ischemic arteriosclerosis and the like, Burger disease), and vascular injury can be mentioned. It can also be used for curing a wound such as skin ulcer and the like or producing an artificial blood vessel. The effect after cell transplantation can be confirmed by a method known per se. For example, when the "disease treatable by angiogenesis" is lower leg ischemic disease, the post-transplantation treatment effect can be evaluated by, for example, examining the lower leg blood flow and necrosis improvement rate. An increase in the blood flow can be measured by measuring the laser Doppler imaging analysis values. In addition, the necrosis improvement rate can be measured by visual observation of limb salvage score. When the disease treatable by angiogenesis is an ischemic cardiac disease, the post-transplant cardiac function can be evaluated, for example, by determining the contractile function and diastolic function. The contractile function or diastolic function of the heart can be determined by various methods used in the art. For example, the contractile function can be determined by measuring +dp/dt value (which decreases as the contractile function decreases) calculated from the mitral regurgitation waveform or left ventricular ejection fraction (% EF, which decreases as the contractile function decreases) and the like. The diastolic function can be similarly determined by measuring −dp/dt value (which increases as the diastolic function decreases) calculated from mitral regurgitation waveform or end-diastolic inner diameter (EDd) and the like (e.g., see FASEB Journal, 18:1392-1394 (2004)).

The agent of the present invention may be the cell population per se of the present invention, which is the active ingredient, or suspended in a liquid medium. The liquid medium may be any as long as it is injectable to human and, for example, phosphate buffer, saline, DMEM as a serum-free medium and the like can also be utilized. The liquid medium may contain a compound preferable for cell survival such as albumin and the like. Preferable examples of the compound including albumin include serum derived from patient.

The cell population as the active ingredient of the agent of the present invention includes vascular endothelial progenitor cell, vascular endothelial cell, anti-inflammatory macrophage, and angiogenic and antifibrotic cells.

The present invention further provides a serum-free medium containing the aforementioned factors, a reagent and a kit for culturing mononuclear cell containing the serum-free medium.

The kit of the present invention may further contain a substance (e.g., antibody) having specific affinity to the cell surface marker of EPC and the like, and/or a differentiation-inducing factor of a hemangioblast or differentiated cell thereof (e.g., factor inducing the differentiation from EPC into vascular endothelial cell). Such kit is preferably used in the cultivation method of the present invention.

EPC of diabetes mellitus (DM) patients shows lower tissue repair and lower regeneration capacity, and the effectiveness of self-EPC cell transplantation therapy for wound healing in DM patients is insufficient. However, by culturing mononuclear cells for about one week by the QQc serum-free culture method of the present invention, a cell population showing loWer tissue repair and lower regeneration capacity due to diabetes can be released from the diabetes environment, and can be re-educated to be a cell population having vascular regenerative capacity and an action to suppress inflammation. That is, by using the cell population of the present invention, a route to the treatment of intractable ulcer and diabetes-related diseases in DM patients is opened.

As reiterated, the cell population obtained by the present invention is a cell population enriched in endothelial progenitor cells as well as anti-inflammatory macrophages, and further with increased regulatory T cells. Therefore, it may also be useful for the prevention or treatment of diseases developed by the function of immune system (e.g., diabetes itself, diabetes-related diseases). The diabetic-related disease here refers to diseases in general which are triggered by vascular disorders associated with the development of diabetes. Examples of such disease include diabetes ischemic diseases (cardiac disease, encephalopathy, four limbs ischemia, refractory ulcer, renopathy, retinal disorder and the like).

The present invention is explained in more detail in the following by referring to the Examples, which are described for explanation of the present invention and do not limit the present invention in any way.

EXAMPLES

In the following Examples, GraphPad Prism5 software (GraphPad Prism5 software, Inc) was used for the statistical analysis of the results. The signed-rank test of Wilcoxon was used for the cell numbers of PBMNC and QQC or the analysis of the ratio thereof. The correlation analysis was performed by linear regression analysis. In other assay, various parameters of those cells were analyzed by the Mann-Whitney U test.

The Kruskal-Wallis test was used for the comparison of 3 groups. $P<0.05$ was taken to show a statistical significance. All values are shown in mean±standard error.

Example 1: Increase of EPC from Peripheral Blood-Derived Mononuclear Cells (1) Preparation of PBMNC and CD34 Positive Mononuclear Cells Using a heparinized butterfly needle set on a 50 ml syringe, peripheral blood (20-100 ml) was collected from healthy volunteers (20-55 years of age). Collection was approved by Tokai University School of Medicine, the Medical Investigation Committee, and the obtained peripheral blood sample was handled according to the biological guideline for human samples. PBMNC was isolated from peripheral blood by the density gradient centrifugation method using Histopaque-1077 (Sigma-Aldrich, #10771) according to the method described in Asahara et al., Science, 275: 964-7 (1997). Isolated PBMNC was washed with PBS-EDTA, and suspended in a buffer to give a cell suspension. The CD34 positive rate of the isolated PBMNC was 0.23±0.03%, and the CD133 positive rate was 0.20±0.07%. In addition, the CD34 positive cell number per 100 ml peripheral blood was $(27.8±4.5)×10^4$, and the CD133 positive cell number was $(23.2±6.9)×10^4$.

CD34 positive cells were purified by an autoMACS separator (Miltenyi Biotec) and using mouse anti-human CD34 antibody coated with magnetic beads and CD34 Cell isolation kit (Miltenyi Biotec, #130-046-702) according to the instruction.

(2) Preparation of Serum-Free Culture Medium

A serum-free medium (hereinafter QQ medium or QQcm) used for the culture was produced using Stemline™ II Hematopoietic Stem Cell Expansion Medium (Sigma-Aldrich, Cat No. S0192) and based on the composition shown in Table 1. To be specific, each of the ingredients shown in Table 1 was aseptically added to a serum-free culture medium to a given concentration.

TABLE 1

|  | supplier and catalog No. | final concentration |
|---|---|---|
| rh SCF | Peprotec, #300-07 | 100 ng/mL |
| rh FL | Peprotec, #300-19 | 100 ng/mL |
| rh TPO | Peprotec, #300-18 | 20 ng/mL |
| rh VEGF | Peprotec, #100-20 | 50 ng/mL |
| rh IL-6 | Peprotec, #200-06 | 20 ng/mL |

In Table 1, "h" means human derivation. "r" shows a recombinant. Other abbreviations are as mentioned above.

(3) Culture of PBMNC

PBMNC isolated by the above-mentioned method was cultured for 7 days in the serum-free medium prepared in (2), using Primaria Tissue culture plate (35-mm Primaria™ tissue culture dish, BD Falcon, #353801) under the conditions of $2×10^6$ cells/2 mL QQ medium per well. The density of the above-mentioned cells in the QQ medium corresponds to about $1×10^6$ MNC per 1 ml of peripheral blood.

As a result of the culture, the number of the cells after the above-mentioned culture (hereinafter to be referred to as QQC, and the above-mentioned culture method is sometimes to be referred to as QQc) to PBMNC before the start of the culture decreased in all test subjects (0.49-fold on average; FIG. 1). The obtained QQC number showed the negative correlation with the PBMNC number per 100 ml of peripheral blood in the linear regression analysis. That is, irrespective of the total number of PBMNC isolated from an equal amount of peripheral blood, about $4×10^7$ cells were obtained on average from 100 ml of peripheral blood.

(4) EPC Colony Formation Assay

Figure 2:
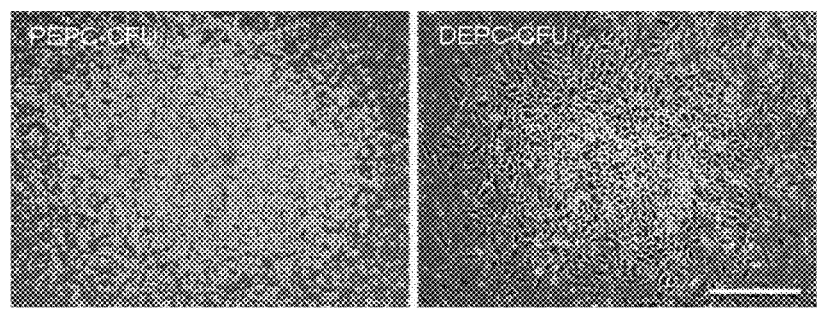
FIG. 2 shows undifferentiated (small-type) EPC colony on the left, and differentiated EPC colony on the right, wherein the bar is 500 μm.

To examine the angiogenesis capacity of the original PBMNC and QQC, adhesive EPC colonies were quantified by EPC colony formation assay (EPC-CFA). EPC-CFA was performed according to the method described in Masuda H. et al., Circulation research, 109: 20-37 (2011). To be specific, in a 35 mm Primaria™ dish (BD Falcon), cells were cultured in a semi-solid medium prepared based on the composition shown in Table 2, and the number of adhesive colonies per dish was measured using a gridded scoring dish (Stem Cell Tec.) at 16-18 days from the start of the culture under a phase difference optical microscope (Eclipse TE300, Nikon). Undifferentiated EPC colony (PEPC-CFU (primitive EPC colony forming unit); FIG. 2, left) and differentiated EPC colony (DEPC-CFU (definitive EPC colony forming unit); FIG. 2, right) were counted separately.

TABLE 2

| component | supplier and catalog No. | final concentration |
|---|---|---|
| MethoCult™ SF$^{BIT}$ H4236 | Stem Cell Tec, #04236 | |
| rh SCF | Peprotec, #300-07 | 100 ng/mL × 1.5 diluted |
| rh VEGF | Peprotec, #100-20 | 50 ng/mL × 1.5 diluted |
| rh basic FGF | Peprotec, #100-18B | 50 ng/mL × 1.5 diluted |

TABLE 2-continued

| component | supplier and catalog No. | final concentration |
|---|---|---|
| rh FGF | Peprotec, #100-15 | 50 ng/mL × 1.5 diluted |
| rh IGF-1 | Peprotec, #100-11 | 50 ng/mL × 1.5 diluted |
| rh IL-3 | Peprotec, #200-03 | 20 ng/mL × 1.5 diluted |
| Heparin | Shimizu Pharmaceutical Co. | 2 IU/ml × 1.5 diluted |
| FBS | JRH Bioscience | 30% |

Figure 3:
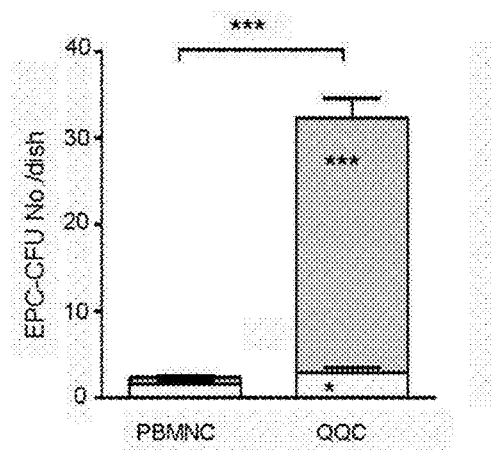
FIG. 3 shows measured numbers of undifferentiated EPC colony (white frame) and differentiated EPC colony (gray frame) after seeding PBMNC (left bar) and QQC (right bar), wherein * and *** respectively show a significant difference (P<0.05, P<0.001) relative to the targets shown in the Figure.

As a result of EPC-CFA, as compared to PBMNC, QQC showed a remarkable increase in the total number of EPC colonies formed per dish, and particularly in the number of differentiated EPC colonies (DEPC-CFU) (13.7-fold and 42-fold, respectively; FIG. 3). Since the frequency of differentiated EPC colony forming cells has been shown to reflect strong angiogenetic activity, the results demonstrate that QQC has revascularization capacity remarkably superior to that of PBMNC. In addition, the number of differentiated colony forming cells and the number of total EPC colony forming cells derived from equal amounts of blood increased by 19-fold and 6.2-fold, respectively, as compared to PBMNC. As for the differentiation level of EPC colony forming cells, 66.4% of the whole EPC colony forming cells were undifferentiated colony forming cells, and 33.6% thereof were differentiated colony forming cells in PBMNC, whereas 8.4% were undifferentiated colony forming cells and 91.6% were differentiated colony forming cells in QQC, thus showing a drastic increase in the ratio of differentiated colony forming cells.

Furthermore, the relationship between the frequency of each EPC colony forming cell in QQC and the frequency of each EPC colony forming cell in PBMNC was examined by linear regression analysis. As a result, the number of differentiated EPC colony forming cells in QQC and the number of total EPC colony forming cells per dish were correlated with the number of differentiated EPC colony forming cells in PBMNC; however, the number of undifferentiated EPC colony forming cells in QQC was not correlated with the number of undifferentiated EPC colony forming cells in PBMNC. On the other hand, the number of undifferentiated EPC colony forming cells in QQC or the number of total EPC colony forming cells was not correlated with the differentiated EPC colony forming cells in PBMNC.

In summary, the frequency of total EPC colony forming cells in QQC was dependent on that of PBMNC. Particularly, the frequency of differentiated EPC colony forming cells in QQC was correlated with the frequency of undifferentiated EPC colony forming cells in PBMNC, and the undifferentiated EPC colony forming cells in PBMNC were differentiated by QQ culture. From the foregoing, it was demonstrated that QQ culture strikingly improves angiogenesis capacity in terms of quantity and quality of the cell.

Figure 4:
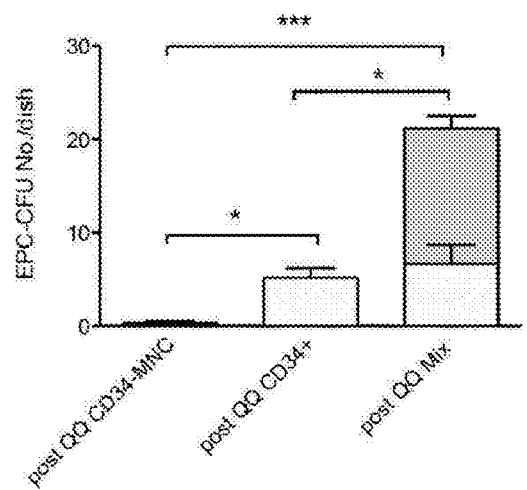
FIG. 4 shows measured numbers of undifferentiated EPC colony (white frame) and differentiated EPC colony (dot frame) formed after 7 days of culture of PBMNC, sorted into CD34 positive and negative cells, in the serum-free medium in the present invention in the presence of CD34 negative, CD34 positive, CD34 positive and CD34 negative cells from the left bar, wherein * and *** respectively show a significant difference (P<0.05, P<0.001) relative to the targets shown in the Figure.

On the other hand, when CD34 positive cells purified in (1) were cultured in the same manner as in (3), and subjected to EPC-CFA in the same manner as in (4), undifferentiated EPC colonies alone were formed, and differentiated EPC colony was not formed (middle bar in FIG. 4). The total number of the EPC colonies formed was smaller than that when PBMNC that were not fractionated with CD34 were QQ cultured. In addition, when CD34 negative cells were cultured in the same manner and subjected to EPC-CFA, EPC colony was not formed (left bar in FIG. 4). When CD34 positive cells were QQ cultured, mixed with CD34 negative cells and subjected to EPC colony formation assay in the same manner, remarkable improvement of differentiated EPC colony formation activity was observed (right bar in FIG. 4). These results suggest that, while CD34 positive cells are involved in the EPC colony formation activity, the presence of CD34 negative cell is important for the activity, particularly, differentiated EPC colony formation activity.

From the foregoing, it was found that EPC number and the number of differentiated EPC colony forming cells can be remarkably increased by subjecting PBMNC to QQ culture without sorting with CD34 expression as an index, as compared to that with sorting. The results mean that QQ culture of mononuclear cells together with CD34 negative cells can increase the ratio of differentiated EPC colony forming cells than QQ culture of separated CD34 positive cells alone, and provides a cell population having strong revascularization capacity. Proliferation of EPC colony forming cells by QQ culture of CD34 positive cells (or CD133 positive cells) inherently showing a very high purity of EPC colony forming cells is predicted easily and the technique therefor has been established. However, the development of a technique that achieves proliferation and differentiation of EPC colony forming cells by directly cultivating mononuclear cells without performing cell separation (CD34, CD133) to increase purity of EPC, and utilizing CD34 negative cells as coculture is an outcome unexpected from the technical knowledge of medical sciences.

Example 2: Flow Cytometry Analysis of Cell Population

To further clarify the characteristics of the cell population obtained in Example 1, expression of cellular surface markers of blood-blood vessel lineage stem cells, blood lineage cells, or blood vessel lineage cells was examined by flow cytometry. Flow cytometry analysis was performed as follows.

The cells suspended in MACS buffer ($5\times10^5$ cells/200 µl MACS buffer) were cultured at 4° C. for 30 min after addition of 10 µl of FC blocking reagent, and dispensed to a reaction tube by equal amounts (100 µl/tube) for the staining thereafter. Each aliquot was cultured together with 2 µl of each primary antibody at 4° C. for 20 min, and washed twice with 1 ml of MACS buffer. The cells were suspended in MACS buffer ($2\times10^5$ cells per 200 µl of MACS buffer). Flowmetry analysis was performed using LSR-Fortessa™ cell analyzer (BD) and FlowJo™ software (Tomy Digital Biology). The antibodies used were commercially available products. For vWF staining, the cells were cultured together with primary antibody, then cultured with biotin-conjugated rat anti-mouse IgG1, and conjugated with streptavidin-PE/Cy7.

Figure 5A:
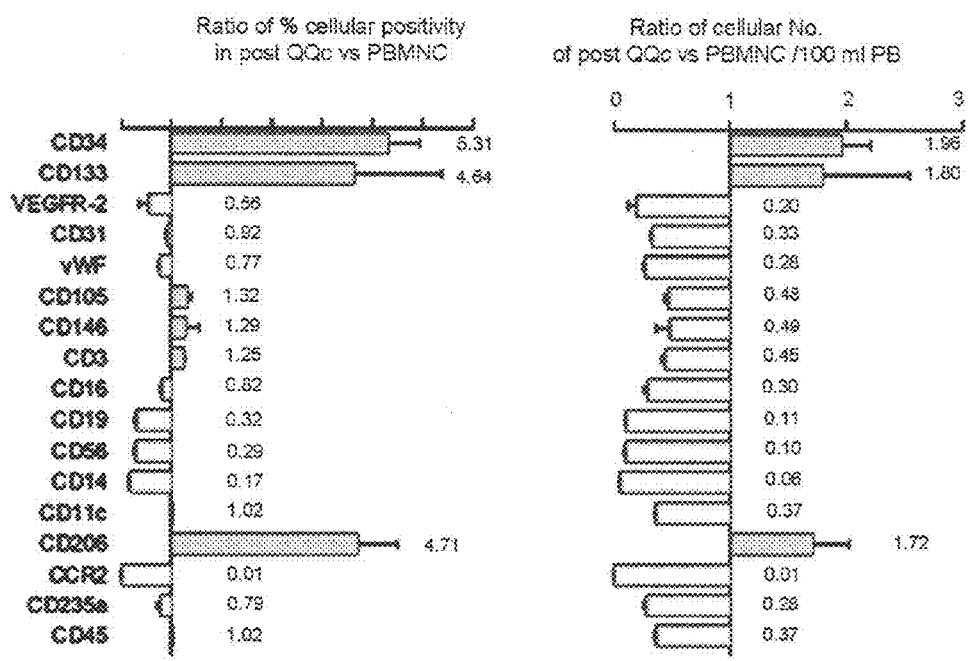
FIG. 5A shows expression of each protein in QQC and PBMNC, which was measured by a flow cytometer and shown in the expression ratio (%) (left) or ratio of positive cell number per 100 ml of peripheral blood (right).

PBMNC or QQC scatter charts were gated into 3 groups based on the cell size, i.e., lymphocyte size, monocyte size, and large-type cell size (FIG. 5A). The cell positive rate of PBMNC or QQC was assumed without fail at each gate, after which each surface marker was gated into 3 cell size regions and measured, and the positive rate in the gated total surviving cell fractions was calculated (FIG. 5A, left side). Also, the positive cell number per 100 ml peripheral blood (FIG. 5A, right side) was calculated using PBMNC or QQC total surviving cell number and the above-mentioned cumulated positive rate.

Figure 5B:
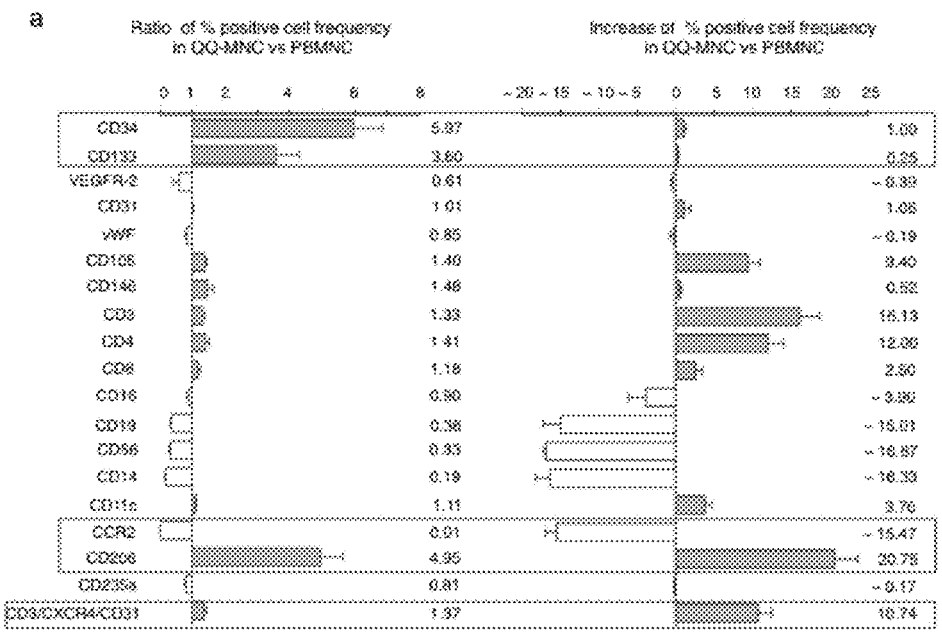
FIG. 5B shows a scatter chart of PBMNC and QQC, which are gated based on the cell size into 3 populations (i.e., lymphocyte size, monocyte size, large-type cell size), which shows positive rates of respective proteins (left) when the total of cells gated into these populations was 100%, and % changes in this case of respective marker expressing cells after QQc relative to the whole cells (right).

Furthermore, the positive rate relative to the total of the cells gated into the above-mentioned 3 groups as 100% was calculated (FIG. 5B, left side), and % change of each marker expressing cells in this case relative to the whole cells before and after QQC was also calculated (FIG. 5B, right side).

As a result of the analysis, the ratio and number of CD34 positive or CD133 positive stem cells drastically increased relative to PBMNC in QQC (for CD34 positive cells, frequency was 5.31-fold, number was 1.96-fold; for CD133 positive cells, frequency was 4.64-fold, number was 1.80-fold), and the ratio and number of positive cells decreased for almost all hematopoietic cell markers (FIG. 5A). The positive rate The marker of endothelial lineage cells showed a slight decrease (0.92-fold for CD31, 0.77-fold for vWF) and 0.56-fold for VEGFR-2. Conversely, for CD105 or CD146, the positive rate increased possibly reflecting the enrichment of in QQC undifferentiated or differentiated colony forming EPC.

What is to be noted is that the parameter (CD206) of anti-inflammatory M2 type macrophage increased to the same extent as the increase of stem cell populations, and conversely, the parameter (CCR2) of inflammatory M1 type macrophage clearly decreased (for CD206 positive cells, frequency was 4.71-fold, cell number was 1.72-fold; for CCR2 positive cells, frequency was 0.01-fold, cell number was 0.01-fold).

The result shows similar tendency to the positive rate relative to the total of the cells gated into the above-mentioned 3 groups as 100%. Specifically, in QQ-MNC as compared to PB-MNC, the ratio of undifferentiated EPC fraction (CD34+ or CD133+ cells) per same viable cell number increased. In addition, the content percentage in the whole viable cells also increased somewhat. This means that undifferentiated EPC fraction is proliferated by QQc (FIG. 5B, the top panel, in square).

the ratio of inflammatory macrophage (CCR2+ cell) per the same viable cell number decreased (left side), and the content percentage (right side) in the whole viable cells further decreased. On the other hand, in anti-inflammatory macrophage (CD206+ cell), all indices decreased (FIG. 5B, lower upper panel, in square).

all of CD3/CXCR4/CD31 as indices of angiogeneic T cells also decreased (FIG. 5B, lower panel, lower side, in square).

Figure 6:
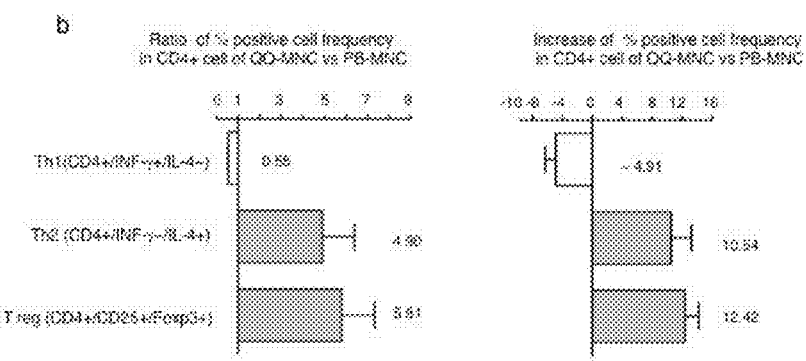
FIG. 6 shows content percentages of helper lymphocyte (Th) subset inflammatory Th1, anti-inflammatory Th2 and regulatory T (T reg) in QQC and PBMNC. The left graph shows ratios of content percentage in QQC relative to content percentage of each Th in PBMNC, and the right graph shows increase or decrease in the actual number of T subset content percentage of QQC relative to PBMNC, wherein N=4-6.

Furthermore, as to the above-mentioned indices in QQ-MNC as compared to PB-MNC, inflammatory T lymphocyte subset (Th1) decreased, and conversely, anti-inflammatory T lymphocyte subset (Th2) and regulatory T lymphocyte subset (T reg) increased (FIG. 6). The left graph shows the ratio of in QQC content percentage relative to the content percentage of each Th in PBMNC. A decrease in inflammatory Th1 (×0.55) and proliferation of anti-inflammatory subset (Th2=×4.9, T reg=×5.81) were confirmed. The right graph shows increase and decrease in the actual number of each T subset content percentage in QQC relative to PBMNC. Variation similar to the left graph was found. N=4-6.

From the foregoing, QQc is considered to simultaneously enrich the stem cell population and provide an anti-inflammatory environment.

Example 3: Comparison of QQC in Healthy Individual and Diabetes Patients

Figure 9:
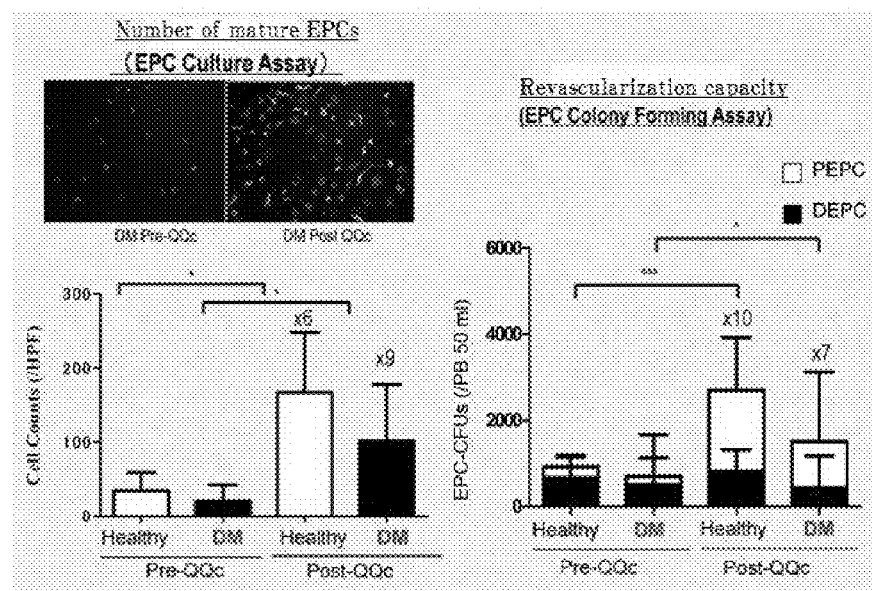
FIG. 9 shows a comparison of changes in the mature EPC numbers and the number of cell colonies having revascularization capacity, when QQc was performed in healthy individuals (Healthy) and diabetes patients (DM). *p<0.05, ***p<0.001

Peripheral blood (50 cc) was sampled from diabetes (DM) patients and healthy individual volunteers, mononuclear cells were collected, and cultured by QQc for one week. The revascularization capacity and the like of the cells before and after QQc were examined by EPC-Colony Forming Assay method (EPC-CFA), FACS, and EPC Assay.
Results: As the results of EPC-CFA in DM patients, the colony number significantly decreased before QQc as compared to healthy individuals, but after QQc, a colony number equivalent to that of healthy individuals was observed (FIG. 9, right side). Therefore, it is considered that the EPC revascularization capacity of DM patients can be recovered to a level similar to that of healthy individuals by performing QQc.

Figure 7:
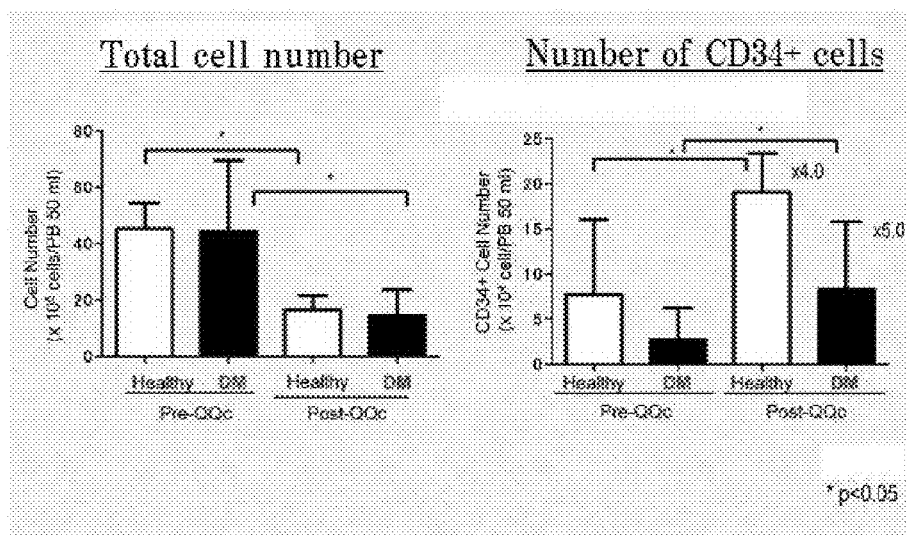
FIG. 7 shows a comparison of changes in the whole cell numbers, and CD34 positive cell numbers when QQc was performed in healthy individuals (Healthy) and diabetes patients (DM). *p<0.05

According to FACS (CD34 antibody), although the whole cell number decreased before and after QQc (FIG. 7, left side), proliferation of CD34 positive cells was also observed in DM patients like the healthy individuals (FIG. 7, right side).

Figure 8:
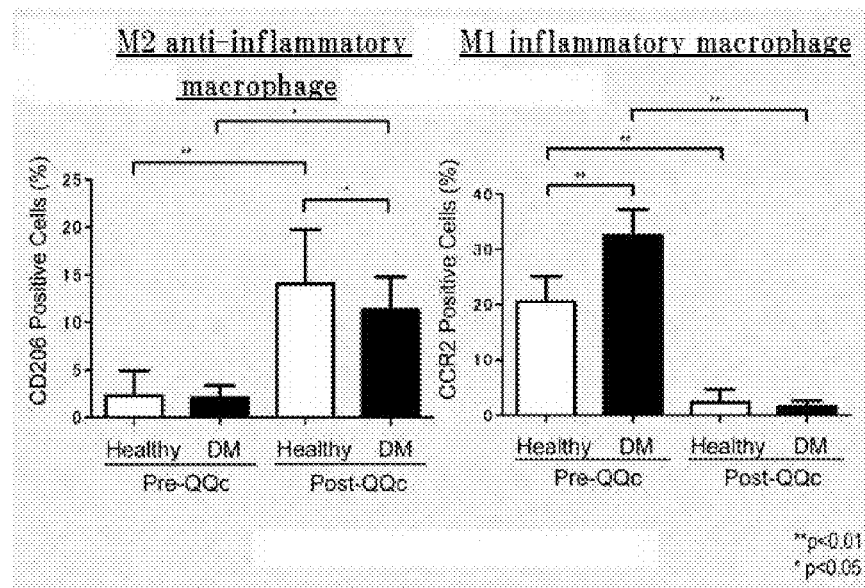
FIG. 8 shows a comparison of changes in the cell numbers of anti-inflammatory macrophage and inflammatory macrophage when QQc was performed in healthy individuals (Healthy) and diabetes patients (DM).

In FACS analysis, the number of M2 macrophage, which is CD206 positive anti-inflammatory cell, dominantly increases after QQc in DM patients and healthy individuals, and the number of M1 macrophage, which is CCR positive inflammatory cell, dominantly decreases (FIG. 8).

In diabetes patients, a scatter chart was formed as in Example 2, they were gated into 3 groups, the positive rate of each surface marker was calculated, and the ratio per viable cell number and the content percentage in the whole viable cells were counted. The diabetes patients also showed a tendency similar to that of the healthy individuals.

Example 4: Real-Time RT-PCR Analysis of Cell Population

The cell population was also analyzed by the real-time RT-PCR method. The analysis was performed as follows.

Total mRNA was isolated by Trizol (Invitrogen), and genome DNA was digested by DNase I treatment. mRNA that underwent DNase I treatment was purified by phenol extraction and ethanol precipitation. 500 ng of purified mRNA was used for cDNA synthesis using SuperScript VILO cDNA Synthesis Kit (Invitrogen). For in vivo colony analysis, cDNA was amplified using TaqMan PreAmp Master Mix (Applied Biosystems), and 45 nM forward and reverse primer mixture. The proliferation conditions used for PCR were as described below: 95° C. for 10 min, followed by 20 cycles of 95° C. for 10 seconds and 60° C. for 4 min. Proliferated cDNA was diluted 10-fold, and the diluted cDNA was used for TaqMan RT-PCR using Eagle Taq Master Mix (Roche), forward and reverse primers (0.3 mM) for cDNA proliferation, and taqMan probe (Sigma Aldrich; 0.25 mM). All primers and TaqMan probe used were commercially available products. For in vitro colony analysis, cDNA diluted 10-fold without a proliferation step was used for TaqMan RT-PCR. All expression levels of the gene were normalized against GAPDH.

Figure 10:
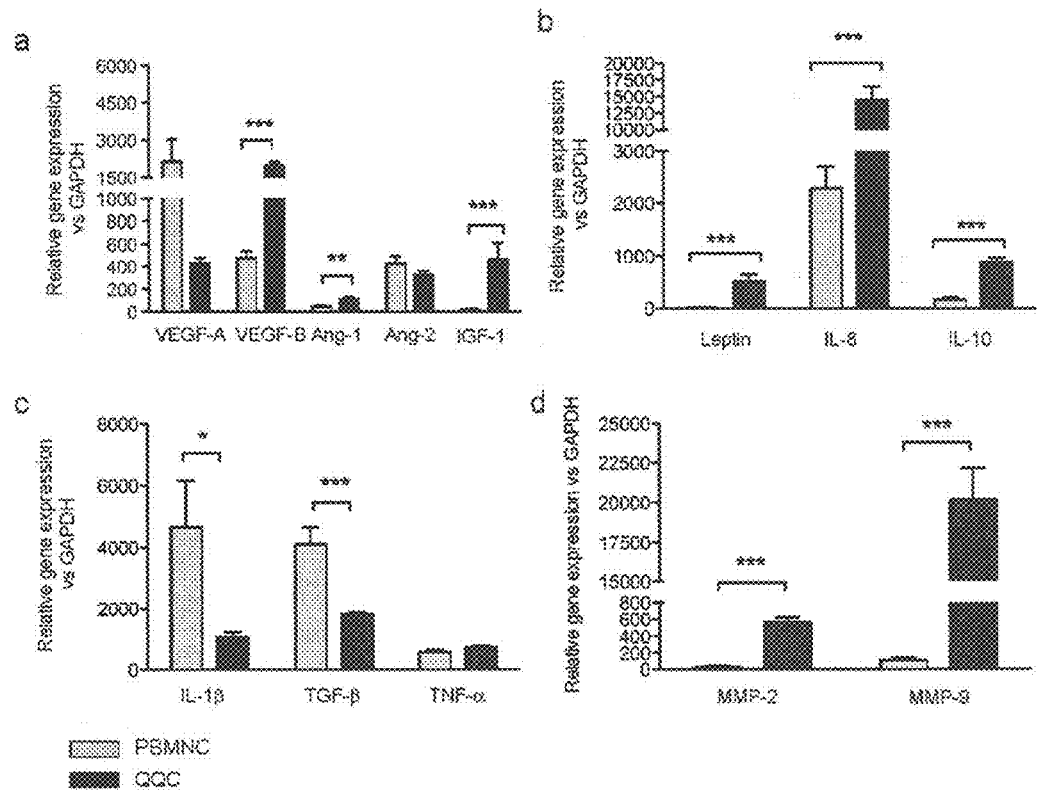
FIG. 10 shows expression of respective genes in QQC (black frame) and PBMNC (gray frame) as measured by quantitative PCR method and shown in the expression ratios vs GAPDH gene, wherein *,  and * respectively show a significant difference (P<0.05, P<0.01, P<0.001) relative to the targets shown in the Figure.

As a result of the analysis, the expression of the factors relating to vascularization/angiogenesis, blood vessel maturing, and anti-inflammation was enhanced in QQC as compared to PBMNC (FIGS. 10a, 10b). As regards the growth factors or cytokines of vascularization/angiogenesis, the expression of VEGF-A showed a tendency toward decrease; however, the gene expression of IGF-1 and angiogenesis cytokines leptin, IL-8, IL-10 was drastically enhanced as if in compensation thereof (21.2-fold IGF-1, 35.9-fold leptin, 6.3-fold IL-8, 5.4-fold IL-10). The expression of blood vessel maturation factors VEGF-B and Ang-1 was also enhanced (4.2-fold VEGF-B, 2.4-fold Ang-1). On the other hand, as for inflammatory cytokines, TNF-α expression showed no change, but the expression of IL-1β and TGF-β was suppressed (0.23-fold IL-1β, 0.44-fold TGF-β; FIG. 10c). The decreased expression of inflammatory cytokines and increased expression of anti-inflammatory cytokine IL-10 in QQC are considered to produce an anti-inflammatory environment in a part of the damaged tissues. Furthermore, the expression of matrix metalloproteinases MMP-2 and MMP-9 known to play an important role in angiogenesis and tissue remodeling markedly increased in QQC relative to PBMNC (22.1-fold MMP-2, 189.4-fold MMP-9; FIG. 10d).

When the expression of each gene in diabetes patients was analyzed in the same manner as above, the expression of VEGF dominantly increased as compared to healthy individuals, and the expression of IL-10 also increased significantly. As for other genes, the gene expression of angiogenetic cytokine leptin was drastically enhanced, and the expression of a blood vessel maturation factor Ang-1 was also enhanced.

Example 5: Evaluation of Angiogenesis Capacity of Cell Population

Next, for evaluation of the angiogenesis capacity of the cell population (QQC) containing EPC and obtained by the method of the present invention, Matrigel assay was performed in vitro. The assay was performed as follows.

As described in Masuda H. et al., Circulation research, 109: 20-37 (2011), cells were cultured in a 1.5 ml tube containing EBM-2/2% FBS (500 μl) added with acLDL-DiI (20 μg/ml; 2-4×10$^4$ in 500 μl) in a $CO_2$ incubator at 37° C. for 30 min and centrifuged at 4° C., 400 g for 10 min. The supernatant was suctioned, cell pellets were washed with 1 ml PBS, and suspended in EBM-2/2% FBS (1.0×10$^3$ cells in 50 μl). Respective labeled cells were resuspended together with HUVEC (in 100 μl EBM-2/2% FBS, EPC:HUVEC=1× 10$^3$:1.5×10$^4$ cells). The mixed cells in suspension were cultured in a water bath at 37° C., and added by 100 μl to matrigel cultured in advance in the well of a 96 well plate (BD Falcon, #354234; 50 μl/well). After 12 hr culture, the number of closed regions formed by HUVEC in a photograph taken by a phase difference optical microscope (×2 HPF) (Eclipse TE300, Nikon) was counted using a Photoshop software. Furthermore, the number of labeled PBMNC or QQC uptaken in the tube in a photograph taken by a fluorescence microscope (IX70, Olympus) was counted using a Photoshop software. The tube number and cell number were counted by a blind trial performed by two people.

Figure 11:
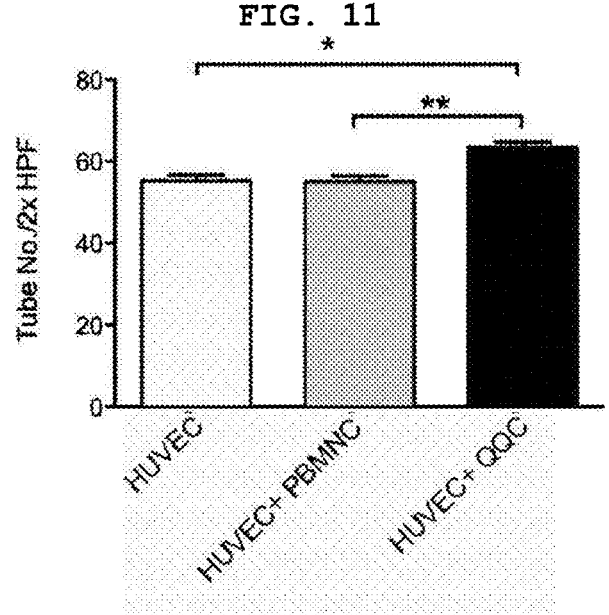
FIG. 11 shows angiogenesis of human vascular endothelial cell (hereinafter HUVEC) without coculture (white frame), with coculture with PBMNC (gray frame), and with coculture with QQC (black frame), wherein HPF shows High power field, and * and ** respectively show a significant difference (P<0.05, P<0.01) relative to the targets shown in the Figure.

As a result, QQC cocultured with HUVEC significantly promoted tube formation at 12 hr after cell seeding as compared to HUVEC+PBMNC or HUVEC alone (tube number per ×2 HPF=63.3±1.43 (HUVEC+QQC), 55.1±1.45 (HUVEC+PBMNC), or 55.3±1.39 (HUVEC alone) (FIG. 11).

Figure 12:
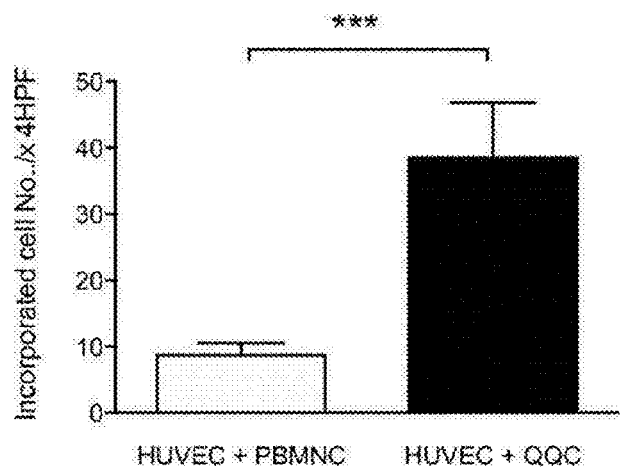
FIG. 12 shows the measured number of PBMNC (white frame) and QQC (black frame), both being labeled with acLDL-DiI and uptaken into blood vessels after coculture with HUVEC, wherein *** show a significant difference (P<0.001) relative to the targets shown in the Figure.

In addition, QQC was found to show a remarkably high ability to uptake into the tube as compared to PBMNC (number of acLDL-DiI stained cells uptaken into tube per ×4 HPF=38.5±8.30 (QQC), 8.72±1.89 (PBMNC)) (FIG. 12).

From the foregoing, it was demonstrated that the cell population obtained by the method of the present invention enhances angiogenesis capacity and intravascular uptake as compared to PBMNC.

Example 6: Transplantation Experiment of Human QQMNC Cell into Ischemia Model Mouse To evaluate usefulness of the cells obtained by the method of the present invention in cell transplantation therapy, a cell transplantation experiment to ischemia model mouse was performed. All animal experiments were performed following the guidelines of Japan and research institutes. The experiment protocol was approved under the guidelines of the animal experiment committee of Tokai University School of Medicine, Isehara campus, which are based on the Guide for the Care and Use of Laboratory Animals of US National Research Council. To reduce the pain and uncomfortable feeling of experiment animals, the maximum attention was paid to anesthesia as well.

In the experiment, 8- to 10-week-old BALB/cAJcl-nu/nu mice (Charles River, Japan) were used according to a previous report (Sasaki K. et al., Proc. Natl. Acad. Sci. USA, 103: 14537-14541 (2006)). The proximal portion of the left femoral artery, including the superficial branch and deep branch, was sutured, and the proximal portion and the distal section of the saphenous artery were occluded with bipolar electric coagulation forceps (MERA, #N3-14). The skin of the part was closed with surgical staples, whereby an ischemic hindlimb model mouse was prepared.

The next day, the cells were suspended in IMDM, and the suspension was intramuscularly injected into 4 sites of the ischemic hindlimb, i.e., two places each of thigh and lower leg (2.5×10$^3$ cells/10 μl/site; total 1×10$^4$ cells/mouse). In particular, a larger amount of the cells was injected to evaluate the differentiation of the transplanted cells into the endothelial lineage in vivo (5.0×10$^4$ cells/10 μl/site; total 2×10$^5$ cells/mouse).

Using Laser Doppler Perfusion Imaging (Moor Instruments), continuous blood flow measurement was recorded for 3 weeks postoperation, and analyzed using Moor ldi Main software (Moor Instruments).

Figure 13:
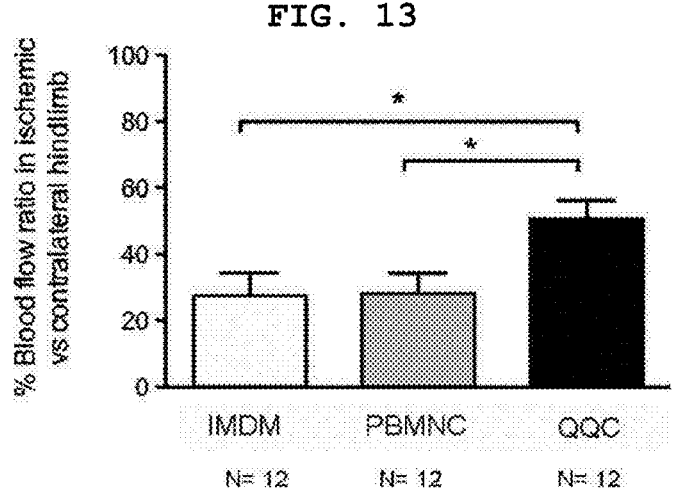
FIG. 13 shows ratios, vs control lower leg, in % blood flow of ischemic mice transplanted with Iscove's Modified Dulbecco's Medium (hereinafter IMDM) (white frame), PBMNC (gray frame) and QQC (black frame), and measured on day 21 by laser dropper image analysis, wherein * shows a significant difference (P<0.05) relative to the targets shown in the Figure, and N shows the number of measured mouse.
Figure 14:
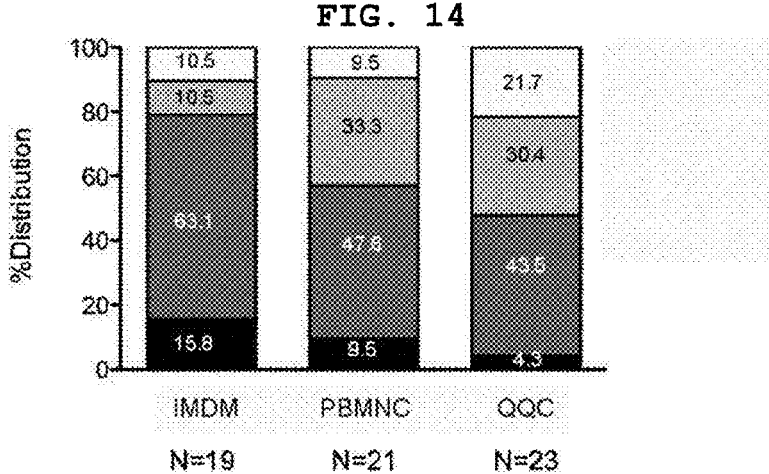
FIG. 14 is a bar graph showing limb salvage (lower leg remaining) scores for each stage in different colors, wherein black shows lower leg necrosis, dark gray shows foot necrosis, pale gray shows toe necrosis, and white shows total remaining, respective bars show the results of transplantation of IMDM, PBMNC and QQC from the left, and N shows the number of measured samples.

As a result, 21 days after ischemia surgery, remarkable recovery of blood flow was observed in the ischemic hindlimb of QQC transplantation animal as compared to the control animal (IMDM injection) or PBMNC injection animal (FIG. 13). The rate of blood flow in the ischemic limb to that in the opposite limb in the QQC transplantation group was 1.85-fold or 1.80-fold as compared to that of the control group or PBMNC transplantation group. In the distribution of the classification of the hindlimb damaged by ischemia, the QQC transplantation group showed the lowest lower leg necrosis frequency (4.3%, 15.8%, 9.5% for QQC transplantation group, control, PBMNC transplantation group, respectively), whereas it showed the highest whole remaining frequency (21.7%, 10.5%, 9.5% for QQC transplantation group, control, PBMNC transplantation group, respectively) (FIG. 14).

From the foregoing, it was demonstrated that the transplantation of the cell population obtained by the method of the present invention can recover, as compared to PBMNC transplantation or without cell transplantation, the blood flow of ischemic animals and further protect tissues from necrosis. Accordingly, the cell population of the present invention is effective for ischemia treatments.

Figure 15:
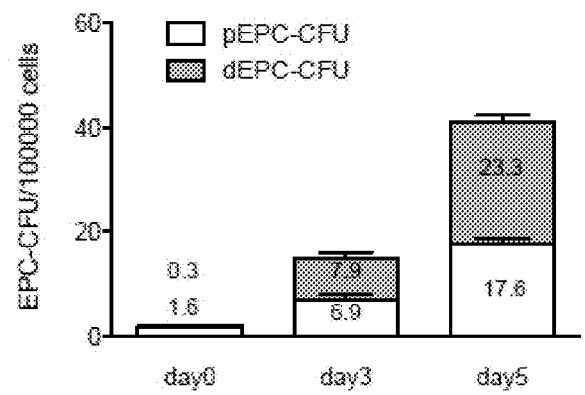
FIG. 15 shows proliferation of EPC along with the number of QQ culture days in mouse EPC-CFA on day 8 after cell seeding. Undifferentiated, differentiated EPC colonies (pEPC-CFU, dEPC-CFU) gradually increased with increasing number of QQ culture days. The numerical values in the graph show each EPC colony number.

Example 7: Transplantation Experiment of Mouse QQMNC Cell into Ischemia Model Mouse (1) Evaluation of Revascularization Capacity of Mouse QQMNC by EPC Colony Assay Intracardiac heparin blood samples were collected from 10- to 12-week-old C57BL6/N (male) mice under pentobarbital anesthesia by using a tuberculin needle, mouse mononuclear cells (MNC) were collected by a density gradient method using Histopaque-1083 and used as mouse PBMNC for the experiment. By a method similar to that for human QQC in Example 1, QQ culture was performed, and EPC colony production capacity of the cells before and after culture was evaluated by EPC-CFA. QQ culture medium=StemLine II, mouse gene recombinants TPO, SCF, Flt-3 ligand, IL-6, VEGF were used. For EPC-CFA, MethoCult™ SF M3236 manufactured by Stem Cell Tec was used, 10% FBS was added and mouse gene recombinant growth factors and cytokines similar to those of human EPC-CFA were prepared at concentrations similar to human. PBMNC and QQC cells (3 days, 5 days after QQ culture) were seeded in a 35 mm Primaria dish each at $1\times10^5$ cells. The colonies were calculated 8 days after cell seeding. Both undifferentiated and differentiated EPC colonies (pEPC-CFU, dEPC-CFU) gradually increased with increasing number of QQ culture days (FIG. 15).

Figure 16:
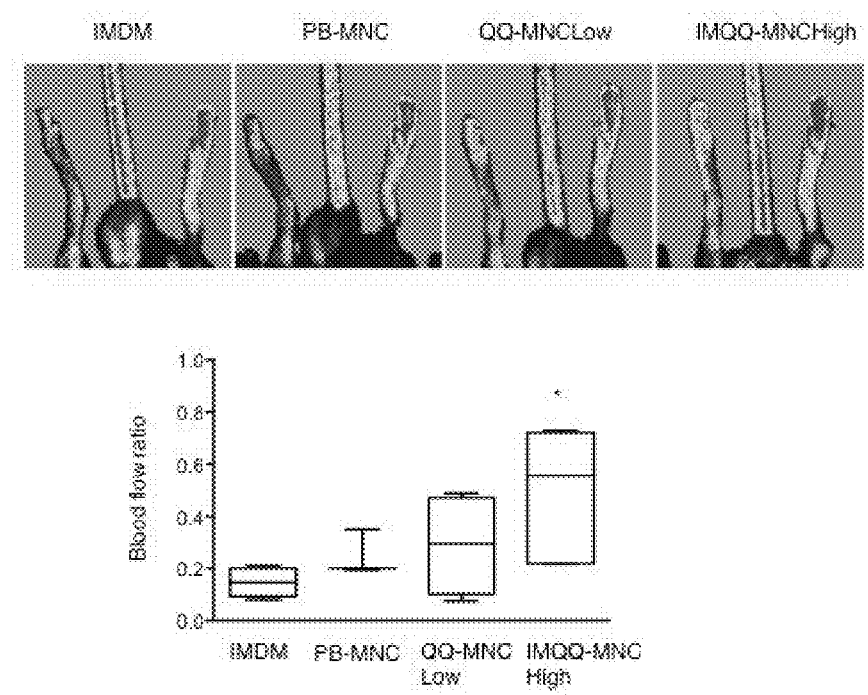
FIG. 16 shows a blood flow improvement effect by QQC transplantation in C57BL6/N mouse lower leg ischemia models.

(2) Evaluation of Blood Flow Improvement Effect by Transplantation of Day 5 QQ-MNC into Lower Leg Ischemia Mouse The cells of QQ culture day 5 were transplanted the next day C57BL6/N (male) mouse ischemia model was generated. The numbers of transplanted cells were PB-MNC=$1\times10^5$/40 microL, QQ-MNC Low=$1\times10^4$/40 microL, QQ-MNC High=$1\times10^5$/40 microL. The control group was an IMDM culture medium as a cell suspension. 20 microL each was transplanted into anterior tibialis muscle and gastrocnemius muscle. At 14 days after generating ischemia, the blood flow was measured by Lazer Doppler Perfusion Imaging in the same manner as in human QQMNC in Experimental Example 5. The QQC cell transplantation group (Low=$1\times10^4$/animal, High=$1\times10^5$/animal) showed a blood flow improvement tendency as compared to the control group (IMDM) and PB-MNC transplantation ($1\times10^5$/animal) group, even though a significant difference was not observed since N of each group was 3 (FIG. 16).

(3) Evaluation of Microvessel Density and Wall Cell Lining Effect

Figure 17:
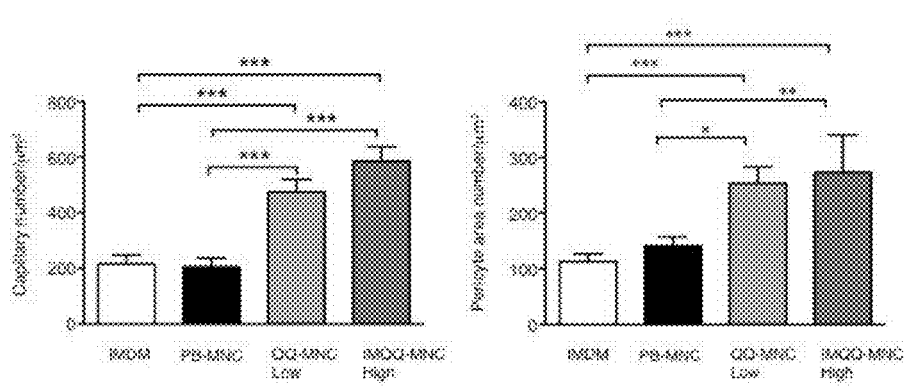
FIG. 17, left graph, shows the measured results of capillary angiogenesis capacity of C57BL6/N mouse lower leg ischemia models by QQC transplantation, as measured by staining with isolectin B4-FITC (Vector Lab). The right graph shows a wall cell region lined with microvessels. The QQC cell transplantation group showed significantly high microvessel density and significantly large vascular region lined by wall cells as compared to non-cell transplantation group (IMDM) and PBMNC ($1\times10^5$/animal), irrespective of the transplanted cell number (Low=$1\times10^4$/animal, High=$1\times10^5$/animal), thus showing high revascularization capacity of QQMNC, wherein the results of transplantation of IMDM, PBMNC and QQC (Low=$1\times10^4$/animal, High=$1\times10^5$/animal) are shown from the left. The actual numbers are, IMDM; capillary count=215.9±32.3, pericyte area=112.6±13.9, PBMNC; capillary count=204.8±32.7, pericyte area=140.8±16.7 and QQCLow; capillary count=474.2±45.4, pericyte area=253.7±29.1, QQCHigh; capillary count=585.2±51.9, pericyte area=273.7±32.4, wherein *, , * show a significant difference (*P<0.05, P<0.01, *P<0.001) relative to the targets shown in the Figure.

After the blood flow measurement at 14 days after generating ischemia, isoectin B4-FITC (Vector Lab) (40 microL) was injected from the tail vein to stain microvessels in vivo, and a sufficient quantity of Pentobarbital was administered intraperitoneally. Under anesthesia, PBS and 4% para-formaldehyde (each 20 mL) were injected from the left ventricle to perform perfusion fixation. After embedding in OCT compound, frozen specimens were prepared by infiltration in acetone cooled in liquid nitrogen. Sections were created from the frozen specimens and subjected to immunofluorescent staining with smooth muscle alpha actin-Cy3 (Sigma-Aldrich). Like human, microvessels and wall cells were observed with a fluorescence microscope and quantitatively evaluated. Both in QQ-MNC low, high, an increase in the microvessel density (FIG. 17, left) and an increase in the number of blood vessels lined by wall cells (promotion of arteriogenesis) (FIG. 17, right) as compared to PB-MNC, non-cell transplantation group (IMDM), and revascularization capacity potentiated by QQ culture was confirmed.

Example 8: Histochemical Evaluation

A tissue section was prepared from the mouse subjected to the transplantation experiment in Example 6, and histochemical evaluation was performed. The protocol thereof is as follows.

(1) Preparation of Evaluation Samples

After 3 weeks from the surgery, 50 μl of isolectin B4-FITC was injected into the tail vein by an insulin syringe. 20 min after the injection, the mouse was euthanized under sufficient anesthesia, immediately thereafter, 20 ml of PBS was perfused by heart puncture, which was exchanged with an equal amount of PBS containing 4% para-formaldehyde to perform fixation. Thereafter, the ischemic hindlimb was dissected, and placed in sucrose/PBS with serial concentrations. Then, the anterior tibialis muscle was dissected, embedded in paraffin and used for the subsequent evaluation.

(2) Evaluation of Microvessel Density (MVD) and Pericyte Recruitment 6-8 μm tissue section samples were sliced from the muscle tissue block, and used for the evaluation of microvessel density (MVD) and pericyte recruitment.

For staining smooth muscle α-actin (SMα actin), tissue sections were deparaffinized, washed with PBS, block with 10% goat serum at room temperature for 30 min, and cultured together with diluted Cy3-conjugated SMα-actin antibody (#C6198, Sigma-Aldrich) at room temperature for 2 hr. After washing with PBS, the sections were mounted using VECTASHIELD HardSet Mounting Medium (Vector Lab, #H-1400), and observed under a fluorescence microscope (Biorevo, #BZ-9000, Keyence). The same protocol omitting the primary antibody was performed as a negative control.

Using a software (VH analyzer, Keyence), MVD was evaluated by counting the capillaries in vivo stained with isolectin B4-FITC in the cross-section of 2-4 mice per each imaged group. At the same time, recruitment of pericytes to the vascular structure was evaluated by counting the area of SMα actin positive cells.

(3) Evaluation of Myogenesis and Interstitial Fiber

Muscle fibers with the nucleus seen in the center by HE staining were imaged by a microscope camera (AX80, Olympus) and myoblasts (Pesce M et al., Circ. Res., 93: e51-62 (2003)) were counted by a VH analyzer. The interstitial fibers in the limb area were morphologically evaluated by Azan staining, and image photographs were analyzed by a VH analyzer (Napoli C et al., Proc Natl Acad Sci USA, 102: 17202-17206 (2005); Sica V et al., Cell Cycle, 5: 2903-2908 (2006)). The number of the evaluated tissue sections was the same as in the above-mentioned (3). In addition, quantitative evaluation was performed by a blind trial by two people.

(4) Immunohistochemical Evaluation of Differentiation of Transplantation Cells into Endothelial Lineage After deparaffinization, microwave was irradiated on the tissue section at 98° C. for 10 min in a target retrieval solution (Dako, #S-1699) diluted with distilled water (1:10). Then, endogenous biotin was blocked by a treatment with Streptavidin/Biotin Blocking Kit (Vector Lab, #SP-2002), and the section was cultured with 5% normal goat serum/PBS at room temperature for 30 min, and then cultured with mouse anti-human CD31 antibody previously reacted with biotinylated goat anti-mouse IgG, and mouse serum (Rockland, #D208) at 4° C. overnight. Lastly, the section was cultured with streptavidin-Alexa Fluor 594 conjugate at room temperature for 1 hr, washed with PBS, mounted using TOTO-3 (Invitrogen, #T3604) in DABCO (Sigma Aldrich, #D2522-25G)/glycerol/PBS, and observed under a laser scanning microscope (Carl Zeiss, LSM510META).

(Results)

Figure 18:
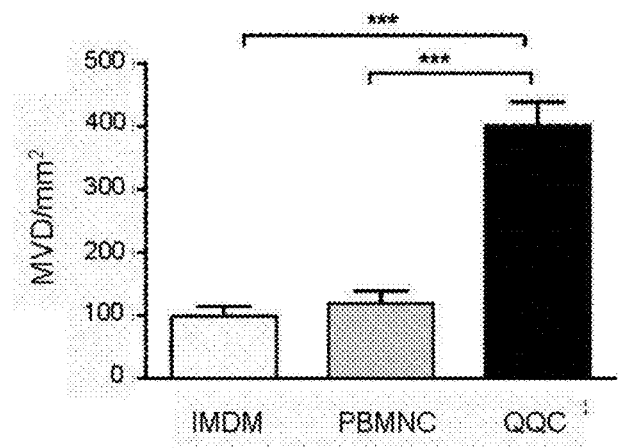
FIG. 18 shows the results of capillary angiogenesis as measured by staining with isolectin B4 antibody, wherein the results of transplantation of IMDM, PBMNC and QQC are shown from the left, and *** shows a significant difference (P<0.001) relative to the targets shown in the Figure.
Figure 19:
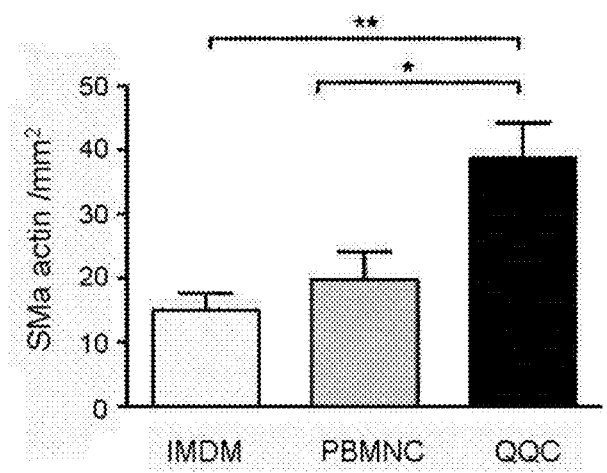
FIG. 19 shows the results of mature angiogenesis (arteriogenesis) as measured by staining with smooth muscle alpha actin antibody (Sigma-Aldrich), wherein the results of transplantation of IMDM, PBMNC and QQC are shown from the left, and * and ** respectively show a significant difference (P<0.05, P<0.01) relative to the targets shown in the Figure.
Figure 20:
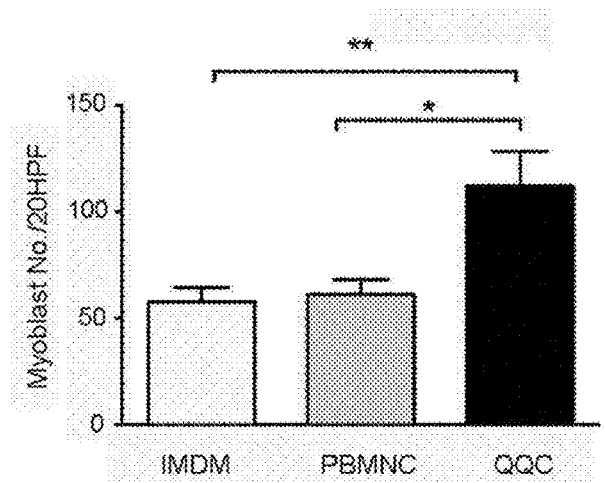
FIG. 20 shows the results of myotube formation as measured by staining tissue fragment with HE wherein the results of transplantation of IMDM, PBMNC and QQC are shown from the left, and * and ** respectively show a significant difference (P<0.05, P<0.01) relative to the targets shown in the Figure.

In the histochemical evaluation of microvessel density (MVD), sections from QQC transplantation group showed remarkably high MVD as compared to the sections derived from PBMNC transplantation group and control (MVD/mm$^2$ was 400.7±37.9 for QQC transplantation group, 98.7±15.8 for control group, 118.9±20.1 for PBMNC transplantation group; thus, 4.1-fold relative to control group, 3.4-fold relative to PBMNC transplantation group) (FIG. 18). As for the recruitment of pericytes evaluated in SMα-actin positive cells, the QQC transplantation group was 2.6-fold relative to the control group, and 2.0-fold relative to the PBMNC transplantation group (SMα-actin positive cell number/mm$^2$ was QQC transplantation group 38.7±5.5, control group 15.0±2.7, PBMNC transplantation group 19.8±4.3) (FIG. 19). Furthermore, in the frequency of muscle fibers, the QQC transplantation group was 1.95-fold relative to the control group, and 1.83-fold relative to the PBMNC transplantation group (muscle fiber/mm$^2$ was QQC transplantation group 112.2±16.4, control group 57.6±7.0, PBMNC transplantation group 61.3±6.8) (FIG. 20).

From the foregoing, it was demonstrated that the cell population of the present invention has remarkably high angiogenesis, artery formation, and myogenesis abilities as compared to PBMNC and control.

Figure 21:
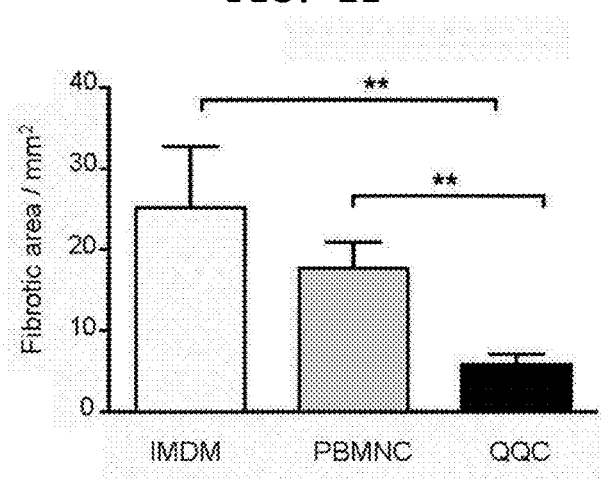
FIG. 21 shows the measurement of fibrosis by Azan staining of tissue fragments, wherein the results of transplantation of IMDM, PBMNC and QQC are shown from the left, and ** shows a significant difference (P<0.01) relative to the targets shown in the Figure.

Furthermore, according to the evaluation of interstitial fiber by using Azan staining, the QQC transplantation group showed a significantly small fibrous region which was 0.23-fold relative to the control group, and 0.33-fold relative to the PBMNC transplantation group (fibrous region/mm$^2$ was QQC transplantation group 5.9±1.28, control group 25.2±7.57, PBMNC transplantation group 17.7±3.18) (FIG. 21).

This shows that QQC transplantation significantly suppresses fibrosis as compared to PBMNC transplantation and control.

Figure 22:
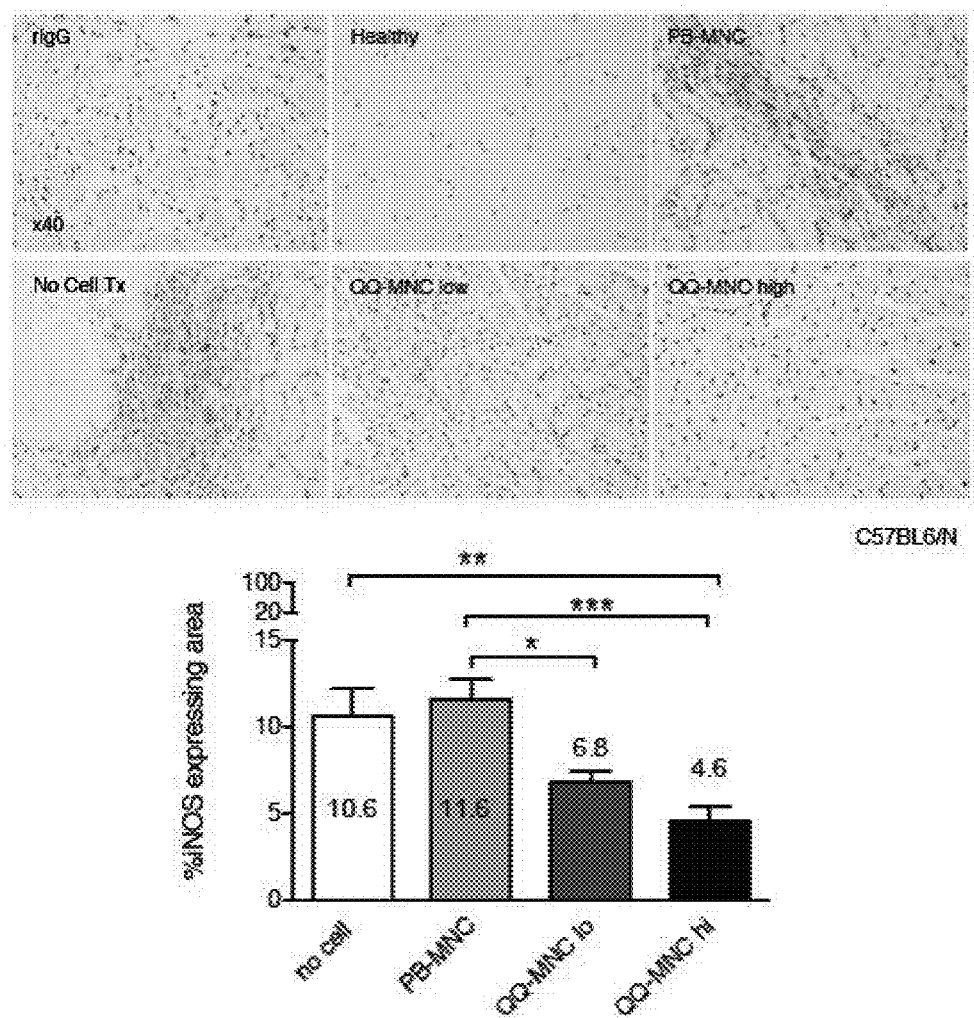
FIG. 22 shows ischemic muscle tissues stained with iNOS antibody. The QQ-MNC transplantation group shows significantly localized inflammation cells.

(5) Evaluation of Anti-Inflammatory Effect by iNOS Expression:

Tissue sections were prepared from the mice subjected to the transplantation experiments in Example 7, and ischemic muscle tissues at 14 days from ischemia generation were stained with iNOS antibody (Abcam) (brown stained portion). The expression of iNOS was enhanced by inflammatory cells, and iNOS staining cells were widely confirmed in non-cell transplantation group and PB-MNC transplantation group, which are control ischemic tissues. In the QQ-MNC transplantation group, it was confirmed that inflammatory cells were significantly localized. Non-cell transplantation group (IMDM)=10.6±1.6%, PB-MNC transplantation group=11.6±1.6%, QQCLow transplantation group 6.8±0.6%, QQCHigh transplantation group 4.6±0.8%, wherein *,  and * respectively show a significant difference (*P<0.05, P<0.01, *P<0.001) relative to the targets shown in the Figure. (FIG. 22)

Example 9: Effect on Ulcer Model (Method)

50 ml of peripheral blood was collected from diabetes patients (5 cases), and healthy individual volunteers (4 cases), human mononuclear cells (MNC) were collected by a density gradient method using Histopaque-1077 and used for the experiments as human MNC. All data were obtained from N=3 (people). Whole skin layer deficient ulcer was generated on the back of Balb/c nude mouse with a 6 mm punch, silicon stent was sutured with 6-0 nylon on the periphery of the ulcer, and an ulcer model with suppressed wound shrinkage was prepared.

Human MNCQQ was cultured by a method similar to that in Example 1, and the cells before and after culture were transplanted into the ulcer model. As a QQ culture medium, StemLine II similar to Example 1, and human gene recombinants TPO, SCF, Flt-3 ligand, IL-6, VEGF were used. PBMNC and QQC cells (1×10$^4$ cells) opacifying PBS 25 ul were transplanted into the ulcer bottom part. After producing ulcer, the ulcer shrinkage rate was measured on photographs taken by Canon Cyber shot on days 0, 3, 7, 10, 14 and wound healing was compared. The ulcer on day 14 was harvested and intratissue blood vessel density was analyzed by Anti-CD31 staining.

(Results)

The diabetes patients (DM) post-QQc cell transplantation group (group A) showed significant shrinkage of ulcer as compared to DM pre-QQc MNC cell transplantation group (group B) and PBS administration control group (group C) (% shrinkage rate; group A 66.92±2.52 vs group B 84.16±3.29, group C 65.61±4.19; p<0.01). In histological evaluation by CD31 staining, DM post-QQc cell transplantation group showed high intratissue angiogenesis as compared to other groups. (CD31 positive blood vessel number; group A 145±28 vs group B 321±58, group C 140±34; p<0.05)

INDUSTRIAL APPLICABILITY

By transplantation of the cells expanded by the method of the present invention, the blood flow and necrosis improvement rate in ischemic diseases was improved. That is, the method of the present invention is considered to be useful for both qualitative and quantitative production of an endothelial lineage cell, and can be a useful method for a cell transplantation therapy targeting a vascular disorder such as ischemic disease and the like.

This application is based on a patent application No. 2012-218206 filed in Japan (filing date: Sep. 28, 2012), the contents of which are incorporated in full herein by this reference.

The invention claimed is:

1. A cell population obtained by a process comprising separating a fraction containing a mononuclear cell from a biological sample, which is collected from a mammal, and incubating the fraction in a serum-free medium, wherein in the medium comprises stem cell factor, interleukin-6, FMS-like tyrosine kinase 3 ligand, thrombopoietin and vascular endothelial cell growth factor, wherein the process does not comprise a step of sorting CD34 or CD133 positive cells, and wherein vascular endothelial progenitor cells and M2 CD206+ macrophages are enriched by the process, wherein the proportion of each type of cell increased 2 times or greater compared to the proportion before the incubation, wherein the vascular endothelial progenitor cells are differentiated EPC colony forming cells, wherein inflammatory M1 CCR2+ macrophages are decreased by the process, wherein the proportion of the inflammatory M1 CCR2+ macrophages decreased to less than 2 times compared to the proportion before the incubation, wherein the total number of all cells decreased after the process when compared to the total number of cells before the process, and wherein the angiogenic activity and anti-inflammatory activity of the cell population increased after the process when compared to the cell population before the process.

2. The cell population according to claim 1, wherein the biological sample is derived from bone marrow, cord blood or peripheral blood.

3. The cell population according to claim 1, wherein the proportion of the M2 CD206+ macrophages increases 4 times or greater compared to the proportion before the incubation.

4. The cell population according to claim 1, wherein the proportion of the M2 CD206+ macrophages increases 5 times or greater compared to the proportion before the incubation.

5. The cell population according to claim 1, wherein differentiation to or proliferation of inflammatory M1 CCR2+ macrophages is suppressed.

6. The cell population according to claim 1, wherein the proportion of vascular endothelial progenitor cells increases 2 times or greater compared to the proportion before the incubation.

7. A method of producing a cell population, comprising separating a fraction containing a mononuclear cell from a biological sample, which is collected from a mammal, and incubating the fraction in a serum-free medium to enrich vascular endothelial progenitor cells, and M2 CD206+ macrophages, wherein the proportion of each type of cell increases 2 times or greater compared to the proportion before the incubation,
- wherein the vascular endothelial progenitor cells are differentiated EPC colony forming cells,
- wherein in the medium comprises stem cell factor, interleukin-6, FMS-like tyrosine kinase 3 ligand, thrombopoietin and vascular endothelial cell growth factor,
- wherein inflammatory M1 CCR2+ macrophages are decreased by the method, wherein the proportion of the inflammatory M1 CCR2+ macrophages decreased to less than 2 times the proportion before the incubation, and
- wherein the total number of all cells decreased after the method when compared to the total number of cells before the method, and
- wherein the method does not comprise a step of sorting CD34 or CD133 positive cells.

8. The method according to claim 7, wherein the separation of the fraction is performed by density gradient centrifugation method.

9. The method according to claim 7, wherein the mammal is human.

10. The method according to claim 7, wherein the mammal is a patient with diabetes.

11. The method according to claim 7, wherein the biological sample is derived from bone marrow, cord blood or peripheral blood.

12. The method according to claim 7, wherein the proportion of M2 CD206+ macrophages increases 4 times or greater compared to the proportion before the incubation.

13. The method according to claim 7, wherein the proportion of M2 CD206+ macrophages increases 5 times or greater compared to the proportion before the incubation.

14. The method according to claim 7, wherein differentiation to or proliferation of inflammatory M1 CCR2+ macrophages is suppressed in the incubation.

15. The method according to claim 7, wherein the proportion of vascular endothelial progenitor cells increases 2 times or greater compared to the proportion before the incubation.

16. A therapeutic agent for treatment of an ischemic disease, comprising the cell population according to claim 1, wherein the ischemic disease is a disease cured by angiogenesis.

17. A therapeutic agent for treatment of refractory ulcers associated with diabetes, comprising the cell population according to claim 1.

* * * * *